US008206911B2

(12) United States Patent
Aguirre et al.

(10) Patent No.: US 8,206,911 B2
(45) Date of Patent: *Jun. 26, 2012

(54) IDENTIFICATION OF THE GENE AND MUTATION RESPONSIBLE FOR PROGRESSIVE ROD-CONE DEGENERATION IN DOG AND A METHOD FOR TESTING SAME

(75) Inventors: Gustavo Aguirre, Philadelphia, PA (US); Gregory M. Acland, Kennett Square, PA (US); Barbara Zangerl, Philadelphia, PA (US); Orly Goldstein, Ithaca, NY (US); Susan Pearce-Kelling, Berkshire, NY (US); Jeanette S. Felix, Horseheads, NY (US); Duska J. Sidjanin, Brookfield, WI (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/715,082

(22) Filed: Mar. 1, 2010

(65) Prior Publication Data

US 2010/0323349 A1 Dec. 23, 2010

Related U.S. Application Data

(60) Continuation of application No. 11/983,870, filed on Nov. 13, 2007, now Pat. No. 7,671,187, which is a division of application No. 11/157,743, filed on Jun. 21, 2005, now Pat. No. 7,312,037.

(60) Provisional application No. 60/581,499, filed on Jun. 21, 2004.

(51) Int. Cl.
*C07H 21/04* (2006.01)
*C12Q 1/68* (2006.01)

(52) U.S. Cl. ...... 435/6.1; 435/6.11; 435/6.12; 435/91.1; 435/91.2

(58) Field of Classification Search ................ None
See application file for complete search history.

(56) References Cited

U.S. PATENT DOCUMENTS

| | | | | |
|---|---|---|---|---|
| 5,804,388 | A * | 9/1998 | Aguirre et al. | 435/6.16 |
| 7,312,037 | B2 * | 12/2007 | Aguirre et al. | 435/6.16 |
| 7,811,761 | B2 * | 10/2010 | Acland et al. | 435/6.11 |

* cited by examiner

*Primary Examiner* — Jeanine A Goldberg
(74) *Attorney, Agent, or Firm* — Hodgson Russ LLP

(57) ABSTRACT

Tools and methods are provided for determining whether or not a dog is genetically normal, is a carrier of, or is affected with or predisposed to progressive rod-cone degeneration. The method is based on the detection of a transversion from G to A at position corresponding to nucleotide position 1298 of SEQ ID NO: 1.

12 Claims, 11 Drawing Sheets

```
   1 CGGCCAGGTG GCACCTCTGA CTCCCAGCCC AAACCTGATG CCAGTGTCCA
  51 CTTCTCCCTG TCGCTCCCTC GCGACCCGC  CCTTCTCAAG ACTTGGTGTC
 101 CCTCTGCAAG TGTGAGAAGA GGTCGGCTCA CCTCTTCCGC TTTGGCTTAT
 151 GTATTTTAAA AATCGTTTTT CAAAGTAGAG AGCCCAGGTG CAGCCCCAGC
 201 TCTGGCCCTC CCTGGGAGCC TGGGCAGGAG ACCCCTTGAC ACCGCTTCCA
 251 TCTCCTTGGA GGGAAGGAAA ATCTAGTGCA GACCYCTGGG GTTTTTGGAG
 301 AGGGCTGGAG GAAGCTGGAT GCTCAGACCC CTGTGTGCTC CACATGCTGC
 351 CTGGGCCACC TCACTGAACC CCTCTGACAG GACACCGAT  GCCTGTGCGG
 401 TGCCCTTCCA AGTGGCTGCT CAGAAGCTTT GCACTGGGAA AGCAAGTATT
 451 CGCTATTTCT ATTTAGTATT TCTATTTAGC TTTATCTCAT CTTTTACAAG
 501 TCTTATGTGT GTTTATTATG CAGGACTGTA TTCGCACAGA TGTGGAAGAT
 551 CTAATGTATG AGCAGATGCA TATACTTATT TCATGAGTGC ACACTTAAAT
 601 CCAGTCTTTT ATGGAAGGGG CTATGGAAAT CAGTAACATT TGGGGAGGAC
 651 TGTCCAGAGG GGAGAACACA ACTGCTCAGC CGCCCTCCA  CTCCCGGCC
 701 TCCCTTGTCT TTCTGGCTTC ATTATC TAAT A TTCTTCCTC CCCTCCCCAT
 751 GGCTCTCCAT GACATCATTG TTCTGCCAAC ACTCAACTTC CAGTTGCTGG
 801 AACATGCTCT GTGCTTTTGT GTCAGCCGCC CCGGAAGAGT CTTCTGTTGG
 851 SGGGGAGGTA ACCTTCCTTG AACACCTGCA AATTCCAATG CCCCCAGCTC
 901 CTCTCCCAAG CATTCCCTGA CACATGCAAC TCCGAAAGTG CTCTGCGGGT
 951 GCCTCTCATC ACCCAAGTCG CTCTACTGTG GTCATTAATG TGACTTGCYA
1001 GCTCAAGTGT CTAGACTAGA AGCCCCTTGA GGGTTAGGCC CAGGTCCTAG
1051 TCACATCTGT ATCCAGAATG GACAGCTTGA TTTACCCTGC CACCGCAGGC
1101 GACAACTTGG GCCCAGTGAG G TTAATCA GT CTGCACAAGG TCGGGTTGGC
1151 TGACCCCA CT AATCA GCTTG AGCCTC CTAA TCC AGTGGCA GCAGGAACCT
1201 CAGGATGGGC AGCAGTGGCT TGTGAGAGCC GGCAGGGCCA TTTTGGCCTT
1251 TCTCCTGCAG ACTCTGTCCG GGAGGGGATG GGGCAGCTGA GCC ATGT R CA
1301 CCACCCTCTT CCTACTCAGC ACCTTGGCCA TGCTCTGGCG CCGCCGGTTC
1351 GCCAACCGGG TCCAACCgtg agaagctgat ggggccatgg gcaggatgg
1401 ggagagagga gaagctaggg ggtgaggggt ggtgcagggg ctgcctggac
1451 ctcctggag  gctggagggc ggggaggatt tgcaggagg  tccagagagg
1501 tttccatca  gagcacgcgg gggcggggc  tcgcaggtgc tccgagactg
1551 gctggagtcc ccgtccccc  agcccaacac ggccaggaga gggggttctg
1601 ggcccgggcg ctgcccacag ctcttccagc ctcttcctcc cgcccacagG
1651 GAGCCCAGCG GAGCAGACGG GGCAGTCGTG GGCAGCAGGT CGGAGAGAGA
1701 CCTCCAGTCC TCGGGCAGgt aaggcagagt ctgggctggg ggaggcaggg
1751 tgcgtcgagg aagcggctgc cctggccgcc ccgaccgtgc ctgggcaggt
1801 acatgagtgc acccgagccg gcgcgccggg gccctcgcc  ccagccaccc
1851 ggtccccgtg tgccggtgg  gcagcctcgg tgtctgtgct ccccgcggc
1901 actggcgcc  csggcctgtc ctctgcaccg cagctgctct gctttgcccc
1951 agtgcggggt ggtccccggg gtccatcggg aaggcgcggg gggaccggag
2001 aggatggggc aggagcagct ccggcggcc  ggctcgctgc ccttccccct
2051 ccccgcggcc cccgctccgc ctcagccgct ccctgcccc  ggccgccggc
2101 gggattcgcc caccggcccc caataggagg cgcaggagcg gcatgacgtc
2151 atcggcaccg cctgccattg gctggcagc  tcctgcgggc aggtcgctgt
2201 ctccagcggc cgaaagttaa ctcttcccta ggccgaagcc atgtggctcc
2251 acaagggggg aagtttgggg aacttctgga ttcttccttc cctgggtgac
2301 cagtgtcctt tgatgttagg ggctcctatg cccaacaaac cacggaaaaa
```

Figure 1A

```
2351  tcaacatgca tttattaaga acataccgtt gtgcgtgttc ttttgtgccc
2401  ccggacccac ctrgtggggg agtcctgtgt gaagggacat tctctcctgc
2451  aaaaggtcta ctagccttct ctcaactcta gtgagacaaa gcacatgatg
2501  cccttgggct ccggggcctg tggctggagg gagtctcccc acagcgctca
2551  gatggctgag ccagtgagcg tgcctgcctg ctggggcacy ccaccggctc
2601  tcctccrggt gtgtaggacc tgcctgggtg ccctcagcc atgtggagac
2651  tggcgagcca tgagaaatga gaatgggaat ctgtctccgt atgcggcccc
2701  aaattcctcy tcggtgctgg gattcctcca agctctgaat rtcaggaggg
2751  cagccctggg catgtccyg agacaggtat tctgggcca cccttccttg
2801  acaatctagg ctagctgaga tggtcatgat actacccaag taggcctgct
2851  ggtgaaatgg gctgacaaag gtgaaatgat gagcactggg cctcacgcag
2901  agcaggccct tgaatgacta gtcctcctg ttgagtttgg gtctggaggc
2951  ggacagccag agtccacatc ctgactccct gcttcctgac cgagagcctc
3001  tgggaaagct atgtgatctt tctatttgta tataaactgg gattaataac
3051  agaatggtgt ggggtgttt gtgaggttca aattgagatc atcctaaagc
3101  acttggcacg aaacagctrt ttaataaatg ccggctagct attctcctgt
3151  tgttacctgg ctcttgatca gtgttctatt cttcccttga ggtctcttaa
3201  acgttaactc acttggaagt tgtaacagcc ccagagggtt ggcaagacaa
3251  gtgtttctat ctcttgttaa tggtggagga aactgaggga aggggaggcg
3301  tcagttttttc actcgaggtc atccatccta tttgtggctg atggcaactg
3351  acttcaggta gtcggtctcc tctacatgaa atgggctgg accctccctg
3401  tcaggagaaa aaagctgaat ctggaccatc tggcccagcc tcgtggggtc
3451  tagccagaag gaagcagttg cctgttaact cccagggacc cagttaactg
3501  gaaaaatcag cctaacatcc aacacctcct gcttcgggtg gctgttgtga
3551  agggctggtc tggggagcag taggcatgac atttctgctc tgcaattcca
3601  cagtcacaaa ttccagctga tttcctggct gctcctaccc ctcagtagtg
3651  gggtgcctcc ctaggcgtgg ggcaaaggga agaagtctgg aaagacggga
3701  aggacgtccc cttcaatcct ctgactccca tgcttttctg tttagAAAGG
3751  AAGAGCCTCT GAAG[TAA]GTC TTCACCCGGT CAGGCGGAGC TCGGCCCCAG
3801  GGAYTGGGAT CAGCTGGCAG AGGCAGgtag ggcaggctg caagccttgg
3851  aaggtagagg gctgggctgg ggacaaggca ggctctgcaa ggcctggcca
3901  tgagggagca gagctccatg gagggtacac agaaggcggg tggcctctca
3951  tcagctcctg cctcaagcct sctgtggtcc aggccatggc gcaaggcttt
4001  gttagtttta agggaagggc gtgtggtgaa gtggtggtca tgctggcact
4051  gtagtgccag aggacttcta agggagaggg tgtgctctgg aatatccatt
4101  ctgcaatgca agccctgcc ttgggatggg aggaagtgcc aatctggttt
4151  tctatttcag TTCAAGTCCC GGCTGGCCTC TTACCCACAA AGCATGCTGT
4201  GGTGGAAGCA GCAGCAGCAG CAAGAAGAAA AATGGGAAAA AGCAGTCATC
4251  AAGAAGGTAG ACTCCTCCCT TTGAGTCCCT GGACCTGCCT GGCCTCCCTT
4301  TGCCCCAGAC CCTGGTGGTG GGGCTCCTGA AGCAAGGCCT GGCTGGGGCA
4351  GGCTGGAGGG CAAAGACGCT CATTGCCCTG GCTTGGGCTC CCTTCCTCTG
4401  AGATCCTGAG GATAGTCTGA GGCAGGCCCA GAGAGGGACT CAGGTTTCTT
4451  ATGGAAGGRC TTCTCATTCA TCCC[TAATAT AAT]CCTTGCA ATGACCCAAG
4501  AAGACTGGGC GTGTTATTAT CCACACTTTT GGAAATGAGG AAACAGAGAG
4551  AGGTTAAGGA ATCTGTCCAG TGTCATCCAG CTAGTTAATC CTGCCCCCCA
4601  CCCCCACCCA CCCCCCGCCC TCCCAGCCTC CTTTGGAGGC TGCAGAGCCC
```

Figure 1B

```
4651  ACACTCTTAC  CCACCAGGGC  ACAGGCCTCT  CTGAAATCAC  CTGGAAGTTT
4701  GCAGCTTGCA  GCTGCTATGT  GAGAGCAGGG  GTTCCACGGG  CCCGGCAGCC
4751  CCAAAGCCTG  TGGTCCAAGG  CTGTGTGGTA  TCAGTTTGCC  ATGGTGGCGC
4801  TCTAGTTTCC  AGGGCACTTG  CCTCTCCCCG  GTCCCCAGAG  CTCACCCCGT
4851  CACCAGCCAC  TCTGCTGCAG  TTCTCAATAA  GAAATGCCAG  CTGGGATCTG
4901  TGACATGTCT  GCCTGCGGCT  GGAAGGAAGC  ATCTCTCAAC  CTGTCCTCTG
4951  AGCGTGTCTG  CGTGCCTGTG  TGCATGCGTG  CGTGTGTTCC  AAAGGGGCAG
5001  TCGCATGTGG  GAAGGGAAGA  AGCCTGACAC  TTGTTCTTGT  CAATCTGCTG
5051  ACTGCTCAGT  ACCACGGCGG  CTCTGCCATT  TCTCCCTCAC  AGTCCTGCTC
5101  GACCCAGAGC  AGAGATCAAA  GCAGATTTCC  GCTTCTGCTC  CCTGAGATCC
5151  AGGCGCAGAC  CTGCAGGCAG  CTGCTCCCCA  CTGTCTGGAA  GCCATTCATC
5201  ATGCAAAGCG  CCTCCCCACC  AAACCCTGC   CTGCACGTGC  ATCRTCCCCC
5251  CACCATCACC  ATCCAGCCCC  CAGGGTGGGC  AGGGAGGTCC  CTGCCTAGCT
5301  GCACACCCCC  CAGGCCATCA  AGAGGCAGGA  GATGGGAGT   TCTCTCGACA
5351  GCAGCCTGTC  TGCCGCCCTG  ACTCCACATC  TGAGGGAAGG  AAGGAAAGGG
5401  TGAGATGCCA  CAGACAGAGG  GGACCACGCT  GAAGCCATGG  GGGAGGGCT
5451  GCTGATCTTG  CCCTGGAAGC  CTCTAGAAGT  AGGGCAGGGT  GGAGGCAGGG
5501  GAAGGGTCAA  ACCAGGGGAA  GGAGCTGTGC  GCTGGAATGG  CGACAGAGCC
5551  CCACCGCCCA  CTCGACATGG  GCCAGGAGTT  CGTGACCACC  TGTCTCAGCT
5601  CCTGTCAGCC  TGTCTTTCTC  CTGCGAGGTG  TTGGCCTTCC  TTGGTGACAG
5651  GGCTGTCGGG  CTGAGGGCCA  GGGGCACCGT  TCCTGGGGCC  CCCATCTKCG
5701  TCCCCGAGCC  CACCTGTGTA  TTCATCCTCT  AATCTGTTTG  CCATGCTCCT
5751  GTCACTTCAG  CCTCGGCTCT  GCTCTCTACC  ATTTCCACGT  TGCCTGCCTC
5801  CTTGCACTAG  TCTGAGGAAT  TGTCAGGCCA  AGGTCACCTG  GCTGGACAGG
5851  GGCTGGCCCA  CGGCCCAGAC  ACACCTCCAC  GAGGCGACAC  CCCTTCGCTG
5901  CACTGTTCTA  GGGACCTGCT  CAGGAGAGGG  TGGCTCCTCT  GGGCCTCGGT
5951  CCCAGAGGGA  AGGAGAGAAG  GGGAAGGGAA  GGGCTGCTGG  CGATGGGGGG
6001  ACTGTGTCGG  CTGGCCTTGG  CGGTTGCCCG  GGCCCTGGCA  GCTGGGGTGC
6051  CATGTGGGCT  GGGCGGGAGG  GGCCCTCTCC  CCCAGGGAGC  AGGCTGGCTT
6101  CGGTGGGAGC  AGATTGTGTT  TACACCTTCC  CCACACACCC  AGCCCACGCT
6151  CGCCTCTTAT  TCCCCGGGAC  TCTCCCACCC  CTGGGCTCTC  TCTGCACCAC
6201  GGGCACGTTT  GCAGCTCCTC  TCCTGCTGCA  GGAAGTTGCC  GCCCTCAGCA
6251  GAGMGCTCCT  CTACAGAAGG  CTGCCAGGGC  CCAGGCGCTC  CCTCCTCGGC
6301  CCACTATCTC  CCGTCGTGGG  GGGGACCCA   GTGTCCCCAA  GAGGCTGAAT
6351  CCACCCACCC  CCCATTTCCT  TGGAAAACAG  CTGCTGCTTG  GAATGGGGG
6401  CAGGAAGGAA  AGCCCGGGGG  GCTTGGCAGA  CTTGACCATA  ATAGGAGGGA
6451  AGGGATTAAG  GGCAACCAGA  GAGAGAGGGC  CGAGAGAGCC  GGGGCGCCTC
6501  TGGCCTCAGG  GTGCATGAGA  TAATGTAGAA  TTTAAGCTCG  GGGAGTCCAG
6551  CTCCAAGCTC  TGGATTTGAA  TCTTGACTCC  ACCATCACTT  TCCAGTTCTG
6601  TGGCCTCGGG  TGGGTTACTG  AATGTAAACC  TGTCTCAGAG  TTGTAAGGGT
6651  TAAATTAGAT  AATGGGTATA  AAGTGCTTCG  CGCACTTAGT  AAGCACGCAG
6701  TATATCTGAG  CCCAGGGTGG  GGGACAGTG   TTTGTGAGCT  GTCAGCCACT
6751  GAACAACTGG  TCACTTTGCA  ACAACCGTAG  GTTCAGAACA  GCTAGTCCTT
6801  TACCTCCTCA  CCCCATGGCC  CTTCCTGCCC  TGTCTTTCCA  CATACACAAC
6851  AGCAGGGTGA  TGGGCAGTTC  TGGAACAAAC  CAGAGCCCAG  CACAGGGCA
6901  CCTGGTAGGA  CCCAGCACCC  GGGAAGCTG   GACGATGGAG  CACCACGGTT
6951  GCYTCTGGGT  GCCTGGAACC  CTGTCCCCAC  CTCCAGTGGG  AGTCCTGACC
```

Figure 1C

```
7001  TGGACATCTT  CCCTCCAACT  GGCTCTGCGW  CCCCAAATGA  ATCTCAGCTC
7051  CTAGAGAAGA  CAGGAGGCCA  TGGCCCTGGT  GCCTTTATGG  TCCTCTGTCT
7101  GAATGCTAAT  CTCTTTACTG  GCTGGAGCCT  GAGTGACAGG  GAAAAGGCGG
7151  TTCTGAGCTG  CAGGGTGGCC  GAGGGCGGCA  GGMGGGAGCA  GGGAGGTGCT
7201  GTTGTCTGCT  ACTTCTGTGG  CTGCTGCCAG  TCTCTCCTRG  AGATGGGAAC
7251  ATGACCAGAG  AGCTAATGAG  GTGGCGGGGG  TGGGGTGGG   GGAGAAAGGG
7301  AGGCAGACGG  AGCAGCTGCA  GCAGCTGCCA  CTGCCCTGTG  TCACCCCAGG
7351  GTGCAAATGC  CACCACGGGG  AGCACCCCGC  CCATCCCGAA  CTGTGTGGCT
7401  GTGCAGATGC  GGGCAGGATG  GTCCTGGGCA  CAGGCCTTGG  TCCAAGACCA
7451  GGCAGGCGTG  GTACTTGATC  TGAGGTGGGC  ATCATGGCAC  AGGAGCTGGT
7501  CCCAGGGGTG  CCCGGGGACC  TTTATAGAAC  CTCAGTCGGG  AAGAAGCCCA
7551  AGACCTTGAG  CCAGAGGGAA  GTAATGCTTC  TTTGTGAGCC  TCAAAAGGAG
7601  GGAAATGGCC  AAGGTTTACA  GTAATATAAT  GACACTAATA  TTATTATTAA
7651  TAATGGCTAA  TGTGTCTCAA  ACGCTTCTTA  CGTGCTAGGC  GCTGTGCCAA
7701  GTGCTTTATT  TATATGCATT  GTCTCATTTA  TGGGGCAGGA  ACTGTTGTCA
7751  GTCTCATTTA  CCCAATAAGG  AAAGTGCTTG  CTCAAGGTCA  CCCACAGTGA
7801  GTAGTGAAGC  AGGACGTGT   TCCCCGGCAA  GGTGATGTAA  AAGCCTGTGA
7851  AGGTRTTGGG  CCTCGAGGAC  ATCCTGGGAG  TGTGACCTGT  CCACCAGGGC
7901  ACAGGGCATG  AGAGCTGGCA  ACCCTCCCTG  GTGATACTGC  CGCTGCTCAG
7951  TCTGCAGAAA  CTCATCATTC  CAGGCTGGAC  CAGACTCTGG  GCCCCGAGGG
8001  CAGTGACCAG  AGCCACCTTT  CCAGGATCTG  TCATGCTCCT  CAGGGAGGAA
8051  GCAGTGGCCA  CTGGCAGGGA  TGACAGATAT  CAAGGTTGTC  ACTCATTGCT
8101  GCTGTTGCTC  TGCTGTTTCC  TCCAACCAGG  GGCAGAGCCC  TGGGGGTAAG
8151  GGAGGGTGGC  AGCCAGCAGC  CCAGCCAGAG  AAGGAGGAGC  CAGAGGAGGA
8201  AGGCTTTGTT  GTTTGTTTTT  ACAGGGGGAY  GGTGCAGGGC  TTTAAGGAGG
8251  TGGCTTCAAG  ACCTGCTGAC  TTTAGCCATA  AACTGGTACC  TAAGGGTGCT
8301  GGACCCTCTC  TGTGGGATAC  ATATGCCCCC  TAGTGGGGAT  TAAGCCTGGA
8351  GGGTGGCTGA  GAAAATTAAA  GCAAACAAA   ACAAAAAAAG  ATTTACTGAT
8401  AGGCTATATG  ACCTCCGAAC  CTGGATAGGA  AGGGCCAGGG  CTGGCCCCCT
8451  GTGTCCCCGA  GATTGCACAA  GCACGCACAG  GTTTAAGACA  ATTTGCAGAA
8501  CCCAGGTGAA  CGAAGCATTG  AAAGAAATTA  TTTAATTTAT  TCCTTGGTCA
8551  TTTATTTAAG  AAGCATGTAT  CGGGAGCCTG  TGATGTACAC  ACCCTGTGGT
8601  AGGTGTTGGA  GTCAGACAGC  AATCAAAGGG  ACGGCGCCCG  ATGTGCCAAT
8651  GAGGACGACA  GAAAGATCCT  GGCCGAGGAG  GCCAGTTGTG  CAAGCTCAGC
8701  CGCTGCCTGC  CACGACTTTT  ACTTCTCTGG  ACCTCAGTCT  CCCCATGTAA
8751  TAGGCAGTGT  TGAACCTAAG  TGGGCTGGTG  CAGAGGATGG  GAAGGACCAC
8801  TGACTACCCT  GGTAAAATGA  AGGGGATGGA  CTTCTTGACC  TCGGGGGGGG
8851  CCCTTCCAGA  TTCAAGACAG  GCTACAGTGG  ACAGTGTTTG  GAGGTGCTGA
8901  CAACGGTGAC  TCGCCCACTC  AGCAAGCGTG  TATGGAGCTC  CTGTATGCCA
8951  GGCATTGTGG  GTGGCAGAAA  TGAAGCRCCC  AGAAAACTGG  ACAAAACTGA
9001  AGAAGCAACA  GACACTTGAC  TACAAGGAAC  ATCCAAGATG  GTGATCCCGT
9051  GACCACCTCA  GCATCTACCT  CCCACAGGTC  CCTGCCTGAG  CACAGGGAGG
9101  GGAAACCCAG  AGGACTGCAG  TGGTCTTGTT  CAGCTGAGGA  GACAAGATCA
9151  GAGCTCAGAA  CAGTGTGCTG  TTCCTAAAGA  TATACACACA  CATCAATGGC
9201  ATCTCCAAAA  CAGACACAAC  GAAGATGATC  CAATGGAGAA  AGAAAAGCCC
9251  TTTTGAGGAA  ACACAAAAAG  TGCTAACCAT  AAAAGAAAAA  AACAGATAAA
9301  TTGGACTTGA  TCAAAATTCT  TGGAAAGACT  GGAAGAGAAT  ACTAGCCAAG
```

Figure 1D

```
 9351  CAAAAATCCG AACAAGGGCC TGTATCCAAA ATATATAAAG AACTTTTACA
 9401  ACTCAATAAG AAGACGACAG CCCAACGGAA AAGTGGGGGA GGGTTTTAAT
 9451  AGACACTTCG CAAGAAACTA GACATATGGC CAATAAACAC ATAAAAAGAT
 9501  ACACAACATC CTAAGCCATC AAGGAAATGC AAATTAAAAC CACAATGAGA
 9551  TACTACTGCA CACTCACCAG AATGGATAAA AGATGGACCA TAATAGACGT
 9601  GGGTGAAGGT GTGGAGCAAC TTGTAACCCT GTCATACGTT GCTGGGAAAC
 9651  CTGTTTGGCA GTTTCTTAGG ATGTAATCCA AGAGGAGTGA ACATGTAGGT
 9701  CCACACAAAG ATTTGTACAG AGATGTTCAC AGCAGTGTTA TTATCAATAA
 9751  TTAGTATCCA AACTGGAAAC AACGCAGATA GCCATCAAGA GGTAAATGGA
 9801  TAAAAAAAAA AAAAAAAAAA AGGAGGCGGT GTATTCATAC AATGGAATAC
 9851  GATTCAGCAA TAAAAAGGCA TTGAGCTACT ATGTGAGCCA TAACACAGGG
 9901  CAATGAGAGA AGCCAGATGC TAAAGAGCAC CTACAGTATG AATCCATTTA
 9951  TAGGAGATTC TAGAACAGGC AATAACTAAT CGGGAGTGGC AGAAAGCAGA
10001  TCAGTGGTTG CCCGGGGCCA GGCTGGATA TGGACACTGT GAAATAGCAG
10051  GTTGGTACCC TCCAGGGGGA TGGAGATGTT CTAAATTGAG ACTGGGGTTG
10101  TGGTTTTATG GGTGTATCAC TGGCTGGACT ATTTTAAATG GATGCACTTT
10151  GTTATATGTA AATTATACCT CAATAAAGAT GACTTAAAGA GTTAAAAAAA
10201  AAAAAAAAAA AAAGAACCAC GAGAATGAAR ACCTGATCCT TGTCTTGCTT
10251  ACAGTCTAGT GAAAACGMCA GATGTGAAAA CAAACAACCA TAAGGCGGTG
10301  AGTAGCCTAA GAAGCATGCT CAAATAACAA GAGTTCTGTT TATGAAGGGC
10351  TCCCTCGCGC CAGACCCACA GAGGTGGCTT GGCGTCACTG TTCTAGAAGT
10401  CCAGATAAGA AAAGAGGCTG AGATGGAGGG GAAGTTGTTC ACGCAGGATT
10451  ACTCAGCTAG AATCAGCAGG CCTGGGACTG GCTCCAAGG CTGCCTGGGT
10501  TCAGAGCAGG TGCCACAGCA GCCTGTGGCA GGACACCGAG CAGAGAGCTC
10551  GGGACTGTTG CAGCTTCTCA GGTGAGACTT TGCGGAGGAG GTATTGACAC
10601  AGGAGTTGGA ATTTGCTCAG CAGAGTAGAG GATGCGGGGA AGGAAATTTC
10651  AAAGCAAAGG GAACAAACAA TATGAGCAAA GGCTGGGCAA CACTTGTGAG
10701  AAGGCAGGGT TCCTGGGAAT GGAGAGACGT GTCCCGAAAA GAGCAGAAGA
10751  GGTCAACAGG ATATTACATG TTCTTCGCAT TCACTTATTT TTTTAAGAAC
10801  CTATTAAGCA ATAATTTTTA CGAGAGGCAA CAGCTCTGCA GGGCAGGCAA
10851  GTGAWGTATG TGCTCTTGGC AAACGCAGGG AAGAACCCAC CGTGATGCCA
10901  AGGTTGCCTC TTTAGGGAAA GGGGTTCTCC CTGTGACATT TCTCCTCCTC
10951  CAGGAGGTTA AGGCTGTGTT CCAGGATCCC AGGTTTCTGC TGAACACCCT
11001  TTGTGGCACT CTTTCACGGT CCTGAGAAAT CCCAGGAGGA AAAAAAAAAA
11051  AACAAAAACC CGCCTGTGCT TTTATGCTGG GCTTTCTGGC TGGAGGAAGT
11101  CAAGTCACTG GAGCGAAGCA AAATGTGTCA CACTGTCATG GTGCGTTCTT
11151  CTGGAAACTC AGCACAGCAG TGAGGTTTGG AGGCTTTGAG GCTGGACTGG
11201  CTGAGGTCAG ATCTCAGCGC TCTTTCACAC TGATTACTTT CCCCTTTCTG
11251  CACTTTGGCT TCTTTAGAAG ATTGCAAAAG AGGGGTGATC ATAAGAGGGC
11301  AGATGTGAGA ATGAAGGGAC AGTACGTGCA ATGTGCTCAG TCAGACTCAT
11351  CGAGTCTGAG ACGTTAATTT AGCCTGTATA GCCTTTTGTA TGACAGTCAG
11401  TCCTCCATAA ATCAGTTTTT TAAAAGAAG GTGCTTAGAG CAGAGCCTGG
11451  CCCAGAGCAA ACATTTAATA GACAGTAGCT TTTGTGTTTT CAAAAAGGTG
11501  ACATGCACAT GTCATCCCTT TTATTTTGCT GTGACCCGTT CTTTCAGAGA
11551  ATTATAATGA AGCGGGATTT GGGACATGTT GATCATATCA TTTAGGATGA
11601  TTGTGACTCT TAACAGAACA CCCAACTTAG GGTGGCTCAA ACAGGAAGGA
```

Figure 1E

```
11651  GATTTCTAAA TCTCACATTC TGGGGCGCCT GGGTGGCACA GTTGGTTAAA
11701  CATTCGACTC TTGGTTTTGG CTCAGGTCAT GATCTCAGGG TTGTGAGATG
11751  GGGCCCTGTG TTGGAGTCTG CGCTCAGCTC ACAATTCTCT CTCTCCTCCA
11801  CTTCTGCCCC TCCTGCCCTC TCTAAAATAA ACATTTGAGG GTTTTTTTAA
11851  AAAGATTTTA TTTAGTTAGT TGAGAGAGAG ACAGACAGAG ACAGAGAGAC
11901  AGAGAGTGAG CATGTGTGAG CACAGGTGGG GAAGGGCAGA GGGAGCAGCA
11951  GAATCCCTGC TGAGCAGGAA GCCCAACACA GGGCTTGATC CCAGGACCAA
12001  GATCAAGACC CGAGCCAAAG GCAGATGCTC ATCCAACTGA GCCAGCCAGG
12051  CAACCCTAAA ATAAATGTCT TTTTTTAAAA AATCATCCTG TGTTTCACTG
12101  AAACTAACAT GCCATTGCTT GTGAGATGCC CCTTGCATTC AGAAATATTA
12151  AAATATAAAA ATGTGTGTCT TTGARTTGAA ACAAAAGGTC TGAAGGTAGG
12201  GGGCTCTAGG ACTGGTAATT TGGCAGTTCA CCATGAGGAC TCTTTGTCCT
12251  TTGTTTCCAC TCTGCCATCG TCAGACCTTA GGCTCTGGCT TTGAGGCAAG
12301  CCTCATGGAT GCAAGATGGC TGCCAGGCC TCAAGCATCA AGTCTTCAGA
12351  GCCTCCCAAA GCCAGAAGAG AGGCTGCTGT TTTTAAAAAC AAGAAAAACT
12401  TTCCCAAACT TTGCTTAATT GCATCACAAA CCCTTTTCTG AATTCCTGGC
12451  AGAAGGAATA GATTTATCAT AAGGGTCTGG TGCCGACTCT TCAAGATTCG
12501  CCCTTAGGGC CGGGGAGGAG CTTGCCTCCA CTGAAGCACC GAGCTCCAGT
12551  TCTGTTGTGA GATGGAGGAA GAACAGCTGT GAGCTGGCAA TGAGCAGCGC
12601  TGCCATACAG ATRAACCGCC TGTGAATCAC CGGTCAACTG TGCCCGACAG
12651  AAGCAGCTGA CTGCTTGGA TATTCCTACC CACCTTCCTG TTCCTATCAA
12701  CAATGGTAGA GCTTCCTCTC CAGGTTAAGA AATTAACCTC CATATTCCAA
12751  AGACTTGGTT TCCTATTAAT GTGGCTTTCG GGTACCGTAT CCAAAATCCT
12801  ATCCGATGG AACCCAGTGA GTTAGCCACC TGAGCACAGC AGGCCAATGG
12851  ACTAGATTTC ACCTCCGTGC TCAGAGCCAA GGCCCCTGA CCGCACCGAG
12901  GACTGTGGCC TTGCTCAGCC TGGGATCTAC TTCTGTCACT GACCACTAGA
12951  TTGGGGGACT CCGTGTCAGT GAATACAGAT CCATGCTAGC CTAGGATGAC
13001  GGCTACGTAA CAATTCCACT GCACATAAAA ACTCAAGTGT CCCAGACCTC
13051  GGGGCGCCTG GCTGGCTTAG GGAGGACTGA CTCTTAATCT CAGAGTCTTG
13101  AGTTCAAGCC CTGTGTTGGG TGTGGAGCCT ACTTAAAAAA AAAAAGAAGA
13151  AGAAGAAGAA GGAGAAGGAG AAGGAGAAGG AGAAGGAGAA GGAGAAGGAG
13201  AAGGAGAAGA AGAAGAAGAA GAAGAAGAAG AAGAAGAAGA AGAAGAAGAA
13251  GAAAGAAGAA GAAGAAGAAG AAGAAGAATT AGAAATCACA ACATTGATGC
13301  TTTGATCTCC ACAGCTCTGA ACTCCGCCT GCTCCTTCAG AAATCTGATG
13351  CGTTCTCTGT TGTCTTTCCA CTGATTTTTT TCTTTTTTTT TTAAGATTTT
13401  ATTTATTTGA CACACAGAGA GATCAGCAGG GGGAGCATCA GAGGGAGAGG
13451  GAGCAGCAGG CTCCCGCTG AGCAGGAAGT CCAACATGGG GCTCAATCCC
13501  AGGACCCTGG GATCATGACC TCAGCCAAAG GCAGATGTTT AACCCACTGA
13551  GCCACCCAGG TGGCCCTGAT TTTTTTTTA AGATTATTTA TTTATTTTAG
13601  GGATCCCTGG GTGGCGCAGC GGTTTACCGC CTGCCTTTGG CCCAGGGCGC
13651  AATCCTGGAG ACCTGGGATC GAGTGCCACA TCGGGCTCCC GGTGCATGGG
13701  GCCTGCTTCT CCCTCTGCCT ATGTTTCTGC CTCTCTCTCT CTCTCTGTGT
13751  GACTACAATA AATTAAAAAA TATTTTTTAA TATTATTTAT TTATTTTAAA
13801  ATATTTTATT TATTTATTCA TGAGAGACAC AGAGAGAGAG GCAGAGATAC
13851  AGGCAGAGGG AGAAGTAGGC TCCCACAGGA CTTGATCCCA GGACCCCAGG
13901  ATCACGACCT GAATCCAAGG CAGATGCTCA ACCACTGAGC CACCCAGGTG
```

Figure 1F

```
13951   TCCCATTAAA GATTATTTAT TTGACAGAGA GAGAGAGAGC AGGAGCAGAG
14001   GGGCACAGGG AGAAGAAGAC TTCCTGCTGA TCGAGGAGCC CGACATGGGG
14051   CTTGAACCTA GAACCCTAAG ATCATGACCC AAGTTGAAGG CAGATGCTTA
14101   ACCAATGGAG CCACCAGGTG CCCCATCCTC CCCTATTTCT GGACTGCCCA
14151   GGCAGTGTGC CCTCTGCCTG CCACTCTTCC TGCTTGTGTG CTCTATTTTT
14201   CAAATAAATA AATTAATTAA AAAATAATAA TCTTGAGGCA CCTGGGTGGC
14251   TCAGTGGTTG AACATCTGTC TTTGGCTCAG GGCGTGATCC TGGGGTCCTG
14301   GGATCGAGTC CCACATTGGG CTCCCTGGAT GGAGACTGCT TCTCTCTCTG
14351   CCTGTGTCTC TGCCTCTCTC TCTCTGTGTG TGTGTGTCTC TCATGAATAA
14401   ATAAATAAAA GGGATCCCTG GGTGGCACAG TGGTTTAGCG CCTGCCTTTG
14451   GCCCAGGGCG CGATCCTGGA GACCTGGGAT CGAATCCCAC GTCGGCTCC
14501   CGGTGCATGG AGCCTGCTTC TCCCTCTGCC TATGTCTGGG ATCCCTGGGT
14551   GGCACAGCGG TTTGGTGCCT GCCTTTGGGC CAGGGCGTGA TCCTGGAGAC
14601   CCGGGATCGA ATCCCACATC GGGCTCCCGG TGCATGGAGC CTGCTTCTCC
14651   TTCTGCCTGT GTCTCTGCCT CTCTCTCTCT CTGTGTGACT ATCATGAATA
14701   AATAAATAAA ATCTTAAAAA AAAAATAAAT AAATAAAATC TTTTTATTAG
14751   ATTTTATTTA AATCTTTTTA TTAGATTTTA ATCTCACTGC GTTTTGCTCC
14801   GGCCTCTCGG CGCCTGCCCA GCCACCCGAG ACATGCCACC TGCGGTGAAC
14851   CTGCTGCTCT TCTACTAGGT GTCCTGTCAG GTGTGAAAGC TCCACTGTAG
14901   ACCGTGGCAT TGTGGCTCCT CTCAAGCCCA GAAGAATGCT CCATGCTCCT
14951   CACACGCACT AGCTGGCAAC CGGTCTGGGA CTCAAGACAG CCCTGCTAGA
15001   GCCCAGAGCC CCCCAGTCTT GCAGCCATCA GCYCCTGCAG CCTCTCCTCC
15051   TCACTCTGCT TGCCATAAAG TGGCTCAAAA CCACGGAACA GGTGCCCATC
15101   ATTCCCCTGA GTAATTTCAT CCCAACCACC CCTGCAAACA CACAAAACCC
15151   TTCTTTGCTC CTCTCCCCCA TGCCCAAAAG CCCTATAGTA AGACTGATGT
15201   ATAGATATAC GAAGTTCAGT ACATCTTAGT GGTGAGAGTA TGGACTCTGC
15251   AGGCTGGCCT CAAACCTTGA CCCCAGCAAT CACTAGTTGT GTGAATTTGG
15301   GAAAGTCACC TCATCTCTCA CTCACCTCAC CTCATCTGCG AAATGCRGGT
15351   AGTGATAGWG CCCTTCAGAG GGCAGCGGTG CACATTAAAC AAATTGGTGT
15401   GCGTTCAGTA CTCCAGGAGT GGACGGCGCA TGGTAAGTGC TACCYGGTAT
15451   CCACTCTCGC TGTTATTCGG CCTGCAGCGG GTCCCTTGCC TCCATCCAAG
15501   CAGCTCTGGG GAACTTCCAC ATTCAAAACT CCCTCTCCGA GTCTGAAAAT
15551   GAAAGGAACT TAGTTTTCAG GGAGAGAGCC CATTCCTCCT TTCCCTATTC
15601   TACAAAACTG TATTCAAGGG CAAGACAGAA ATGCAAGGGC CAGTTTCATA
15651   AGACAGATGT TACTGCCAAG TGAGTCAATG ATTATCTGTT GTGTACGTGG
15701   GCAGAGGCAG AGGAATAACA ACCAGACTCT GGGAGGCAAT TAAAAAGAAA
15751   AAAAAAAAAA GTAAAAGAGT GTCTCATGGA GCGCCTGGGT GGCTCAGTCC
15801   GTTAAGCCTT GGACTTTTGG TTTCCCCTCA GGTCATGATC TCAGGGTCGT
15851   GGGACCCAGC CCTGGGGCGG GCTCTGTGAT CAGTGGGGAG CCTGCTTGAG
15901   ATTCCCTCCT TCTGCTGTGC ACACTCTCTC TCTAAAATAA ATACGTCTTT
15951   AGAAGAGCAA GCGAGCGAGA GATGCTTCCC GCCTAGAAGA GCTTACAATC
16001   AAATCAAGGG AGGCAAACAT AAACAAGTGT GGCAACTTGA TAATAAGCAC
16051   CTGCGACCTA TGGCCATACA CAGAATAACA TAACCCAGAC TAAATGCCAC
16101   TGCATAGTCA CTAGCGGGTT GATGACAACG GGGGAGGCT AATGCTGAAA
16151   AGGCCTTTCT GTCTTATAAG TTTAAACTAA TTTCTGGGGG CACCTGGGTG
16201   GCTCTGGTTG AGCATCTGCC TTTGGGTCGT CGTCCCAGGG TCCTGAGATC
```

Figure 1G

```
16251  GAGTCCCTCA  TCCGGCTCCC  AGCCCCGTAG  GAGCCTGCTT  CTCCCTCTGC
16301  CTCTTCCTCT  CTGTCTCTCA  TGAATAAATA  AATAAAAATT  TTAAGGGATG
16351  CCCGGGTGGC  TCAGCGGTTT  AGCGCCTGCC  TTTGGCCCAG  GGTGTGATCC
16401  TGGGGTCCCG  AGATCGAGTC  CCACATCGAG  TCCCACATCG  AGTTCCGGGA
16451  TCGAGTCCCT  GCAGGGAACC  TGCTTCTCCC  TCTCCCTGTG  TGTGTGTCTC
16501  TCTCTCTTTC  TGTATCTCTC  ATGAATAAAT  AAAGAAAATC  TTTAAAAATA
16551  AATAAATAAA  AACAGTATTT  AAAAAAATGA  ACTAATTTCC  AAGTAGGTGT
16601  AAATTCTGGC  TCGGACTAGT  GAATGGCTCT  GGCTCTGCTG  CATCACCCAC
16651  CGCCAGGGCT  CTGGGCCGCT  CCGAGCCCCG  CTCGCCGGCG  CCCCCTGCCG
16701  CCCGGGCCTC  CGCCTTCAC   CCCAACCCGC  AGGGCGGCGG  AGCCCTAGGC
16751  CCAATCGGCC  CCGGGAACCT  GCCGCCTCTT  CTCTAGCGCA  ACCCAGCACC
16801  CAGATGACCC  CTTTTCCGCC  CCAGGTGCAG  TCCGGCCGGG  CCCTGGTGTC
16851  CTCACCCGTT  CCCCTAGGGA  GACCCCTCTC  GAACCTTCTG  CGCCACCCTA
16901  CTCTACGCCA  GGGAAAATCT  GTGCACTCAG  TAGATAAATG  CTTGTAACTG
16951  AAGCAACCGT  CTCCGTGGCT  CCAGAATCGC  GCTGAGGATG  CTGCTGCCGC
17001  ACCCCCACCT  CCCCCGGCTC  CGGCGGAGGT  TGTTTGGACT  ACACTTCCCA
17051  TGAGGCCCCT  CTCAACATCG  CGATAACTCT  CGCGAGACCG  CTGGGAAGAG
17101  TTGTGCGCAG  GCGCAGCCCC  GCCTTCTTGT  CGAGGCAGGC  CGCGTGGCCG
17151  GCAGTCATGG  CGGCTCCTTG  CTGGCCCGAC  CGGGACAGGG  AGTCTGGAGY
17201  CTCTGGCTGT  GGTAAGGTTG  TCGAGGCGGG  CAGACGGGAT  CGTCCTTGGC
17251  CCGGCGCTAG  TTCGCTCGGC  CTCCCTTTCC  TCGGGGCGG   GATGATGACG
17301  GTAAAGCCGG  TCTTCCTCGT  AGGGTGGTTG  GGTTAGTTGA  GATGCTGGAT
17351  CGGAAAACGC  TTTCTGAGCG  GCGCGAGTGT  TGACGATCGA  AGGGAGAGAG
17401  CTCAGGCCCC  CCTTGGAGTC  AGAGGGCCCC  TCCTGGGGGG  GGGGGTCCTC
17451  CAGCCTGTGC  AGCCCCGTGT  GTGCCCTGCG  GGTCTCCCGG  GCCCGCCCAC
17501  GGGAGGCTGC  CGGTGGTAGT  TCTTAATCCA  CATCAAGTGT  TAACGTGAGG
17551  GTCCTGGAGT  GCCCCGAGGT  CGGCCCTGGT  CAGTGGTTCG  TATTCAGTCC
17601  TACAGATAGT  AGTAAAGGGG  CTTGTAGATT  TTGGAAAGCC  ATAATGCTCT
17651  GCGCCCTACC  TTCCATGTTC  ATTTTTTTTC  CCCTCTCTCT  TCCCGTACAG
17701  GGTTTTCTTT  GCGTCGCAGA  CCTGCAGGTT  GAAGCTTAAA  AGTAGCGAAT
17751  GGGGAGCCCT  GTGAAATGGG  TAAGGATGGG  TGCTGGCAGG  GCCCGGGTGG
17801  TGACCAGAAG  TGAGAAAGTC  GAGATGGTGG  GCAGGCCTGC  CACACCCGGC
17851  CGCCGCACGC  TTTACTTTAC  TAATTTTATT  TTTTTTAAA   GRTTTAATTA
17901  ATTAATTAAT  TAATGATAGG  CAGAGACACA  GGCAGAGGGA  GAAGCAGGCT
17951  CCGTGCCGGG  AGCCGACGC   GGGACTCCAG  GATCGCGCCC  TGGGCCAAAG
18001  GCAGGCGCCA  AACCGCTGAG  CCACCCAGGG  ATCCCACTTT  ACCGATTTTA
18051  AGTTCGGTTC  TTAGGAACAC  GTGGACGCAC  GCATCCGGTT  AGGGTGAGAA
18101  GAAAACGGAC  CCGGGTCCTG  GAAGCGAGCA  GGGCCTTGCC  AGTGTGACTC
18151  GGCGCCGCTA  GGTGTCACTG  TTTGGATTCA  AACCGGTTGC  CGCGCACGAG
18201  GTTGGCGGGG  AGGCTTAGGA  AATGGGCTTC  GGTGGGGTTT  GGAAGTATTT
18251  GTGGATGATT  TAAAGTTATC  TTTGTCTTAA  AGGGCTCTTT  TGTGAAGAGT
18301  TTTGATGCGT  TGAGGCTCAG  CTTTTTTTTT  TTTTTTTTTT  TAAGGTTTGT
18351  ATTCATTTTT  TCACAGAGAG  GCAGAGGGAG  GAGAAGCTTG  CTGCCTGCAG
18401  AGAGCAGGAT  GCGAGACTCG  ATCCCTGGAT  TTCGGGATCA  CGCCCAGAGC
18451  CAAAGGCAGA  CACGCAACTA  CTGAGCCACC  AGGCGTCCC   GAGGCCCCAG
18501  CTTCTTAAAT  AACCAATCTT  GAGAATAACA  TCTTGACCTC  ATTTCTCTTA
18551  GAATATACTT  TGTTACATTT  CCCTTAGAGA  TTAAAGGTGT  TG
```

Figure 1H

```
  1  AGTGGCAGCA GGAACCTCAG GATGGGCAGC AGTGGCTTGT GAGAGCCGGC
 51  AGGGCCATTT TGGCCTTTCT CCTGCAGACT CTGTCCGGGA GGGGATGGGG
101  CAGCTGAGCC ATGTRCACCA CCCTCTTCCT ACTCAGCACC TTGGCCATGC
151  TCTGGCGCCG CCGGTTCGCC AACCGGGTCC AACCGGAGCC CAGCGGAGCA
201  GACGGGGCAG TCGTGGGCAG CAGGTCGGAG AGAGACCTCC AGTCCTCGGG
251  CAGAAAGGAA GAGCCTCTGA AGTAAGTCTT CACCCGGTCA GGCGGAGCTC
301  GGCCCCAGGG AYTGGGATCA GCTGGCAGAG CAGTTCAAG TCCCGGCTGG
351  CCTCTTACCC ACAAAGCATG CTGTGGTGGA AGCAGCAGCA GCAGCAAGAA
401  GAAAAATGGG AAAAAGCAGT CATCAAGAAG GTAGACTCCT CCCTTTGAGT
451  CCCTGGACCT GCCTGGCCTC CCTTTGCCCC AGACCCTGGT GGTGGGGCTC
501  CTGAAGCAAG GCCTGGCTGG GGCAGGCTGG AGGGCAAAGA CGCTCATTGC
551  CCTGGCTTGG GCTCCCTTCC TCTGAGATCC TGAGGATAGT CTGAGGCAGG
601  CCCAGAGAGG GACTCAGGTT TCTTATGGAA GGRCTTCTCA TTCATCCCTA
651  ATATAATCCT TGCAATGACC CAAAAAAAAA AAAAAAAAAA AAAAA
```

Figure 2

IDENTIFICATION OF THE GENE AND MUTATION RESPONSIBLE FOR PROGRESSIVE ROD-CONE DEGENERATION IN DOG AND A METHOD FOR TESTING SAME

This application is a Continuation of application Ser. No. 11/983,870, filed Nov. 13, 2007, now U.S. Pat. No. 7,671,187, which is a Divisional of U.S. application Ser. No. 11/157,743, filed on Jun. 21, 2005, now U.S. Pat. No. 7,312,037, which in turn claims priority to U.S. provisional application No. 60/581,499, filed on Jun. 21, 2004, the disclosures of each of which are incorporated herein by reference.

This work was supported by Grant No. EY006855 from the National Institutes of Health (NIH). The Government has certain rights in the invention.

FIELD OF THE INVENTION

The present invention relates generally to a class of genetic diseases, observed in canines, termed progressive rod-cone degeneration ("prcd"). More particularly, the invention relates to a gene and a single nucleotide mutation in the gene associated with progressive rod-cone degeneration in dogs.

BACKGROUND OF THE INVENTION

Progressive Retinal Atrophy (PRA) is a heterogeneous class of retinal disorders that share a broadly similar clinical disease phenotype, and affect the dog (*Canis familiaris*) (Aguirre, 1976). The clinical features include: initial night blindness followed by reduction in photopic vision leading to complete blindness; reduction in retinal vessels, and retinal thinning; abnormalities in an electroretinogram ("ERG"); and the development of cataracts. Diseases of this group are typically inherited by means of an autosomal recessive gene defect although dominant and X-linked forms of PRA also are recognized (Kijas et al., 2002; Zhang et al., 2002). PRA may be classified into developmental and degenerative diseases. The developmental class comprises several genetically distinct diseases expressed cytologically in the immediate postnatal period when visual cells in the canine retina begin to differentiate (Acland et al. 1989). In contrast, the degenerative class represents defects in which photoreceptor cells degenerate after having differentiated normally—this class includes the specific disease termed progressive rod-cone degeneration (prcd). This specific form of PRA is an autosomal recessively inherited, late-onset retinal degenerations affecting several different breeds of dog (Aguirre and Acland, 1988).

Mutations at the prcd 'gene locus account for all of the autosomal recessive late-onset hereditary retinal degenerations recognized to date in dogs. By cross-breeding experiments, it has been determined that the prcd gene locus is responsible for progressive retinal atrophy in poodles (toy, and miniature), cocker spaniels (American, and English), Labrador retrievers, and Portuguese water dogs (see, e.g., Aguirre and Acland, 1988, Aguirre and Acland, 1991; Pearce-Kelling et al., 2002). Cross-breeding experiments suggest the same mutation in the F04 gene (which is gene responsible for prcd) is also present in several other breeds either in dogs affected with prcd; or carriers of the disorder. However, based on clinical and genetic parameters consistent with disease caused by mutations at the prcd gene locus, other breeds of dogs suspected of having prcd as the form of observed progressive retinal atrophy include akita, basenji, border collie, English mastiff, English springer spaniel, Havanese, lowchen, samoyed, standard wirehaired dachshund, Tibetan terriers, Bernese mountain dog, and miniature schnauzer. Depending on the breed of the dog, different mutations responsible for allelic variants of the prcd gene locus can regulate the rate of progression, but not the phenotype, of photoreceptor degeneration.

Clinical diagnosis of prcd disease is complicated by the need for sophisticated testing methods such as ERG, and by the late onset of the disease. The age at which the disease can be diagnosed by current methods may be past the dog's reproductive life. For example, in English cocker spaniels, progressive retinal atrophy may be diagnosed by ERG at three years of age, and by opthalmoscopy at 5-8 years of age. This late age of diagnosis results in the dissemination of the undesirable trait within the population, and an increase in the disease frequency.

The estimated prevalence of progressive rod-cone degeneration differs among affected breeds. It is believed that approximately 2% of Labrador retrievers more than 2 to 3 years old are affected with progressive rod-cone degeneration; if so, then the proportion of Labrador retrievers expected to be heterozygous at the prcd locus could be as high as 24%. In poodles and cocker spaniels, the disease rate is higher than that observed in Labrador retrievers, and hence, the carrier rate would be expected to be higher. From the results of a survey of Portuguese water dogs, the calculated carrier frequency is approximately 40%.

Traditional measures for controlling inherited diseases in a population included performing "test" matings to identify carrier dogs, and to eliminate the identified carriers from breeding programs, thereby reducing the frequency of genetic disease in a breed. In a test mating, the dog being evaluated as a potential carrier of the genetic disease is mated with a dog known to be affected with the disease. Progeny are then observed for absence or presence of the disease, and a litter equal to or larger than 6, all of which are unaffected offspring, typically "clears" the dog from being a carrier. While test matings have been effectively used for breeds having large litter sizes, and for diseases which are early onset, such a procedure is not practical for reducing the frequency of prcd. In addition to the disadvantages of test matings such as great expenses in time and effort incurred to clear a dog and that affected dogs can be born if the dog to be evaluated is a carrier, test matings are not particularly suited for detection of carriers of prcd because of the late onset of clinical symptoms associated with the disease, and because some of the breeds affected have small litters (too small for establishing statistical probability).

Although the gene carrying the mutation or mutations that cause prcd has previously been unknown, genetic linkage studies in prcd families have shown that the gene that causes the disease in dogs resides on the centromeric end of canine chromosome 9, an area that is homologous to the telomeric end of the long arm of human chromosome 17 (Acland et al., 1999; Sidjanin et al., 2003).

In spite of the extensive efforts in the art to find the gene responsible for prcd, until now the gene has remained elusive. Identification, isolation, cloning, and sequencing of the prcd gene would enable the design and manufacture of products useful for the diagnosis and screening for prcd. Therefore, there has been an ongoing need in the canine breeding industry for a genetic test that permits direct identification of dogs that have the prcd form of progressive retinal atrophy (e.g., before detectable onset of clinical symptoms), as well as permitting the genotyping of dogs at risk for prcd to establish if they are affected, carriers or genetically normal.

SUMMARY OF THE INVENTION

The present invention provides an isolated nucleic acid molecule encoding a novel disease-associated canine gene, referred to herein as the F04 gene. The invention further provides the F04 gene having a G to A mutation at position 1298 of SEQ ID NO:1. This transversion is associated with and is indicative of prcd.

The present invention also relates to a method for identifying dogs, which are genetically normal, carriers of, or affected with prcd disease. Genetically normal dogs are those in which both alleles of the F04 gene have G as the nucleotide at a position corresponding to nucleotide position 1298 of SEQ ID NO:1. Affected dogs or predisposed dogs are those in which both alleles of the F04 gene have A as the nucleotide at a position corresponding to nucleotide position 1298 of SEQ ID NO:1. Carrier dogs are those in which one allele of the F04 gene has G and the other allele has A as the nucleotide at a position corresponding to nucleotide position 1298 of SEQ ID NO:1. A change of G to A in the F04 gene at a position corresponding to nucleotide position 1298 of SEQ ID NO:1 is termed herein as the "prcd mutation". The nucleotide position 1298 in SEQ ID NO:1 also corresponds to nucleotide position 115 in the cDNA sequence shown in SEQ ID NO:3

The method comprises the steps of obtaining a biological sample from a dog and testing the biological sample to identify whether or not G is present at a position corresponding to nucleotide position 1298 of the F04 gene. In one embodiment, the method comprises detecting a G to A mutation at a position corresponding to nucleotide position 1298 of SEQ ID NO:1 in one or both alleles which is indicative of a dog that is a carrier of or a dog that is affected with (or predisposed to) prcd respectively.

The present invention also provides a method for selecting dogs for breeding. This method comprises obtaining a biological sample from a dog, testing the biological sample for the F04 gene having a prcd mutation in one or both alleles, and eliminating dogs with the prcd mutation from a breeding stock, or breeding the dogs with the prcd mutation with genetically normal dogs.

BRIEF DESCRIPTION OF THE FIGURES

FIG. 1 shows the genomic sequence of the canine F04 gene (SEQ ID NO:1).

FIG. 2 shows the sequence of the cDNA from the canine F04 gene (SEQ ID NO:3).

FIG. 3 is a representation of restriction endonuclease digestion of amplified products from genetically normal, carrier dogs or dogs affected with prcd.

DESCRIPTION OF THE INVENTION

Figures 3A, 3B:
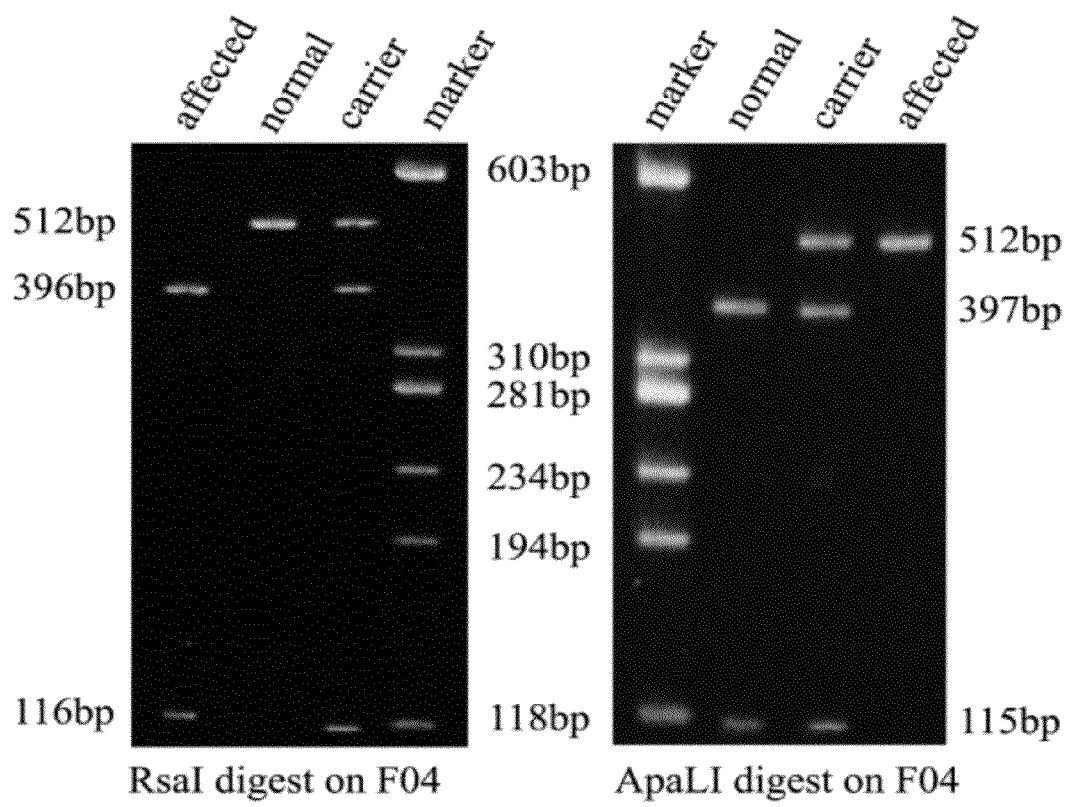
FIG. 3A shows digestion with the restriction endonuclease RsaI and FIG. 3B shows digestion with restriction endonuclease ApaLI.

This invention provides a nucleic acid molecule encoding a novel F04 gene located on chromosome 9 in dogs. The sequence of the wild type F04 gene is presented in FIG. 1 and details pertaining to the sequence are as follows.

Explanation of the Genomic Sequence

The genomic sequence of the F04 gene is 18592 bp long. The sequence listed in SEQ ID NO:1 includes, all polymorphisms identified heretofore. Nucleotide exchanges are shown in italics as follows: W=A/T; M=A/C; R=A/G; Y=C/T; S=C/G; K=G/T. Insertion/deletions are shown in italics and underlined. Sequence for the affected and alternative allele for all polymorphisms shown in the sequence are presented in a separate Polymorphism table (Example 2). Microsatellite at position 13,146-13,278 bp is also shown in italics and is boxed.

In the public domain canine genome sequence assembly (canFam1) dated July 2004 (http://genome.ucsc.edu/cgi-bin/hgTracks?org=Dog&db=canFam1&hgsid=42443361), the F04 genomic sequence (SEQ ID NO:1) is localized incorrectly to chr18:26,568,308-26,586,788. We believe this is incorrect, as we have established through our BAC contig, and by FISH and meiotic linkage mapping that, as predicted by comparison to the homologous regions of the human and mouse genomes, this canine genomic region is properly located on CFA9. This discrepancy does not affect the accuracy or the utility of the tests described herein.

Throughout this sequence, proposed exons and UTR regions are shown in upper case letters and defined exons are bolded. Intronic regions are in lower case letters.

Exon 1: bp 1-1,367

Includes a TATA box at position 727-731, three CRX binding sites at positions 1,122-1,128; 1,159-1,165; 1,177-1,183 and the ATG signal indicating the start of the ORF at position 1,294-1,296 all underlined and boxed.

The prcd mutation at position 1,298 is shown in italics, bold and boxed. The mutation is a change of G to A and is shown as "R".

Exon 2: bp 1,650-1,718
Exon 3: bp 3,746-3,826

Includes the stop codon at position 3,765-3,767 shown underlined and boxed.

Exon 4: bp 4,161-4,256
3'UTR: bp 4,257-18,592

Within this region there are several potential adenylation signals which are pointed out underlined and boxed. The region entitled 3'UTR has also been shown to contain regions of alternative splicing (indicated in bold), which further defines within this region:

Exon 5a: bp 4,806-5,399
Exon 5b: bp 4,839-5,399
Exon 5c: bp 5,093-5,399
Exon 6: bp 6,558-6,665
Exon 7: bp 6,927-7,164
Exon 8: bp 7,547-7,720
Exon 9: bp 12,275-18,592

The deduced amino acid sequence of a putative protein encoded by the F04 gene, based on the sequence of SEQ ID NO:1, and assuming a start site at position 1294 is shown below as SEQ ID NO:2.

```
                                              (SEQ ID NO: 2)
Met Cys Thr Thr Leu Phe Leu Leu Ser Thr Leu Ala

Met Leu Trp Arg Arg Arg Phe Ala Asn Arg Val Gln

Pro Glu Pro Ser Gly Ala Asp Gly Ala Val Val Gly

Ser Arg Ser Glu Arg Asp Leu Gln Ser Ser Gly Arg

Lys Glu Glu Pro Leu Lys-
```

In this case, the prcd mutation would result in cysteine (the 2nd amino acid) being replaced by tyrosine.

The F04 cDNA Sequence (see SEQ ID NO:3)

Several splice variants of the F04 gene have been identified, all of which include the same ORF. The shortest full length splice variant is 695 bp long; the cDNA (SEQ ID NO:3) for this variant of the F04 gene is shown in FIG. 2. Those skilled in the art will recognize that potential future identification of additional exons, that do not alter the F04 ORF as described herein (such as a noncoding exon 5' to exon 1, or 3' to exon 3), will not affect the demonstrated association of the prcd mutation with PRA or detection of the prcd mutation as described herein.

Explanation of the cDNA Sequence:

The cDNA sequence embeds the ORF of 165 bp, located at position 111-275 (both start and stop codon are highlighted in bold). The mutation is located within the ORF at position 115 shown in italics, bold and boxed (Normal allele=G; mutant allele=A). Other polymorphisms (for examples: Y=C/T, nt 312 SEQ ID NO:3, Polymorphism #55, Table 1; and R=G/A, nt 633 SEQ ID NO:3, Polymorphism #57, Table 1) in the 3'UTR are not disease associated because both alleles have been identified on normal chromosomes. All cDNAs that include the F04 ORF incorporate exon 1 (bp 1-184), exon 2 (bp 185-253), exon 3 (bp 254-334) and exon 4 (bp 335-695), however, partial cDNAs obtained using different primer sets establish that different splicing variants in the 3'UTR can include at least exons 5 and 8 as defined in the genomic sequence. Other features are the same as in the genomic DNA.

Detection of the prcd mutation in the F04 gene can be carried out in any suitable biological sample obtained from a dog. In a preferred embodiment, the biological sample is any tissue containing genomic DNA. Suitable sources of biological sample include blood, hair, mucosal scrapings, semen, tissue biopsy, or saliva. In one embodiment, the biological sample is blood.

Dogs carrying the prcd mutation in F04 gene may be detected by testing either the DNA or the RNA, using a variety of techniques that are well known in the art. The genomic DNA used for the diagnosis may be obtained from a biological sample as described above. The DNA may be used directly or may be amplified enzymatically in vitro through use of PCR (Saiki et al., Science, 239:487-491 (1988)) or other in vitro amplification methods such as the ligase chain reaction (LCR) (Wu and Wallace, Genomics, 4:560-569 (1989)), strand displacement amplification (SDA) (Walker et al., PNAS USA, 89:392-396 (1992)), self-sustained sequence replication (3SR) (Fahy et al., PCR Methods Appl., 1:25-33 (1992)), prior to mutation analysis. The methodology for preparing nucleic acids in a form that is suitable for mutation detection is well known in the art.

Detection of DNA sequence mutations, such as the prcd mutation in the F04 gene, can be accomplished by a variety of methods including, but not limited to, restriction-fragment-length-polymorphism detection based on allele-specific restriction-endonuclease cleavage (Kan and Dozy Lancet, 2(8096):910-912 (1978)), hybridization with allele-specific oligonucleotide probes (Wallace et al., Nucl Acids Res., 6:3543-3557 (1978)) including immobilized oligonucleotides (Saiki et al., PNAS USA, 86:6230-6234 (1989)) or oligonucleotide arrays (Maskos and Southern, Nucl Acids Res., 21:2269-2270 (1993)), allele-specific PCR (Newton et al., Nucl Acids Res., 17:2503-25 16 (1989)), mismatch-repair detection (MRD) (Faham and Cox, Genome Res., 5:474-482 (1995)), denaturing-gradient gel electrophoresis (DGGE) (Fisher and Lerman et al., PNAS USA., 80:1579-1583 (1983)), single-strand-conformation-polymorphism detection (Orita et al., Genomics, 5:874-879 (1983)), RNAase cleavage at mismatched base-pairs (Myers et al., Science, 230:1242 (1985)), chemical (Cotton et al., PNAS USA, 85:4397-4401 (1988)) or enzymatic (Youil et al., PNAS USA, 92:87-91 (1995)) cleavage of heteroduplex DNA, methods based on allele specific primer extension (Syvanen et al., Genomics 8:684-692 (1990)), genetic bit analysis (GBA) (Nikiforov et al., Nucl Acids Res., 22:4167-4175 (1994)), the oligonucleotide-ligation assay (OLA) (Landegren et al., Science, 241:1077 (1988)), the allele-specific ligation chain reaction (LCR) (Barrany, PNAS USA, 88:189-193 (1991)), gap-LCR (Abravaya et al., Nucl Acids Res., 23:675-682 (1995)), and radioactive and/or fluorescent DNA sequencing using standard procedures well known in the art.

Further, several new techniques have been described including dynamic allele-specific hybridization (DASH), microplate array diagonal gel electrophoresis (MADGE), Pyrosequencing™, the TaqMan system as well as various DNA "chip" technologies such as the Affymetrix polymorphism chips. These methods require amplification of the target genetic region, typically by PCR. Still other newly developed methods, which may not need PCR are based on the generation of small signal molecules by invasive cleavage followed by mass spectrometry or immobilized padlock probes and rolling-circle amplification. Several of the methods known in the art for detecting specific single nucleotide polymorphisms are described in U.S. Pat. No. 6,720,141 and the description of these methods is incorporated herein by reference.

As will be appreciated, the mutation analysis may also be performed on samples of RNA by reverse transcription into cDNA therefrom.

Any one or any combination of such techniques can be used in accordance with the invention for the design of a diagnostic device and method for the screening of samples of DNA or RNA for prcd gene mutation of G to A at a position corresponding to nucleotide position 1298 of SEQ ID NO:1 of the F04 gene. Thus, in accordance with the invention, there is provided a nucleic acid based test for prcd gene mutation which comprises providing a sample of a dog's DNA or RNA and assessing the DNA or RNA for the presence of the prcd mutation. Samples of dog DNA or RNA (or genomic, transcribed, reverse transcribed, and/or complementary sequences to the prcd gene) can be readily obtained. Through the identification and characterization of the F04 gene as taught and disclosed in the present invention, one of ordinary skill in the art can readily identify the genomic, transcribed, reverse transcribed, and/or complementary sequences to the prcd gene sequence in a sample and readily detect differences therein.

Accordingly, in one embodiment, the present invention provides nucleic acid fragments for detection of nucleic acids wherein the mutation is present. In general, the detection methods are based on DNA hybridization techniques, wherein hybridization to DNA sequences is performed under stringent conditions such that a change in one nucleotide can be detected. Optimal stringency is normally obtained by adjusting the reaction temperature and/or salt concentration so that the probe will only hybridize to its specific target, although those skilled in the art will recognize that alternative methods of optimizing for target specific hybridization are readily available.

Thus, allele-specific probes can be hybridized under conditions that are sufficiently stringent so that there is a significant difference in the intensity of the two alleles. Preferably, the hybridization conditions are sufficiently stringent so as to produce an essentially binary response (i.e., the probe hybridizes to one but not the other allele).

Further, primers can be designed which hybridize to a target sequence such that upon amplification, products are generated which contain the prcd mutation site. The primers should be long enough to be useful in reactions such as polymerase chain reaction (PCR) process or as probes in a ligase chain reaction (LCR) procedure. Generally fragments which are at least twelve bases in length are considered suitable for amplification reactions. The amplification products can be subjected to restriction endonuclease treatment and identified by denaturing gradient gel electrophoresis so as to distinguish between the amplification products from the two alleles.

Suitable fragments useful for hybridization can be identified from the sequence of the F04 gene presented herein or may be identified by hybridization to the nucleic acid sequence of the F04 gene (SEQ. ID. NO:1) or the cDNA (SEQ ID NO:3) under stringent conditions as described above.

By using the tools and method described herein, dogs which are genetically normal for the disease (G in both alleles), carriers of the prcd disease (G to A transversion in one allele) and dogs which are affected by (or predisposed to) progressive rod-cone degeneration (G to A transversion in both alleles) can be identified. Upon identification, such affected (or predisposed) or carrier dogs can be eliminated from the breeding stock. Alternatively, dogs which are affected (or predisposed) with prcd, or carriers of the prcd disease, can be mated with genetically normal (without the G to A transversion) dogs to ensure the absence in the litter of dogs affected with prcd.

This invention can be used for any breed of dog including, but not limited to, akita, American cocker spaniel, American eskimos, Australian cattle dog, Australian stumpy tailed cattle dog, basenji, Bernese mountain dog, border collie, Chesapeake bay retriever, Chinese crested, English cocker spaniel, English mastiff, English springer spaniel, Entlebucher mountain dog, Finnish lapphund, German shorthaired pointer, giant schnauzer, Havanese, Labrador retrievers, lowchen, miniature poodle, miniature schnauzer, Nova scotia duck tolling retriever, Portuguese water dogs, samoyed, silky terrier, spitz, standard poodle, standard wirehaired dachshund, Tibetan terriers, toy poodle. Because the identical prcd mutation in the F04 gene has been demonstrated to be present in, and cause PRA in so many different breeds, this mutation appears to have arisen long before the differentiation of the dog population into these different breeds. It is thus expected that the same mutation will prove to be present in other breeds of dogs in which its presence is not currently recognized.

The invention will be further understood by the following examples, which are intended to be illustrative and not restrictive in any way.

EXAMPLE 1

We have produced a retina specific canine EST library from 16 week old beagles. One set of 5 individual overlapping EST clones formed a contig which mapped to the previously specified CFA9 area (Sidjanin et al., 2003) and was therefore further investigated. This sequence contained the later defined F04 exon 8 (see below, EST clone contig, 1085 bp).

From sequence information from the above EST contig, and that of hypothetical human genes located within the corresponding region of the human genome sequence as deposited in GenBank, two primers were designed for RT-PCR: Forward: 5'-caccttggccatgctctggc-3' (located at the end of exon 1)-SEQ ID NO:4 Reverse: 5-aatgcatataaataaagcacttggc-3' (located in exon 8)-SEQ ID NO:5

RT-PCR was performed from a 3.3 week normal dog resulting in a 707 bp product (clone 9) spanning the end of exon 1, exon 2, exon 3, exon 4 and exon 8.

Comparative in silico analysis of canine genomic sequence from our BAC contig (see example 2, below), with public domain human and mouse genomic sequence, identified a highly conserved region, contiguous with the 5' end of clone 9, that included potential CRX binding sites followed by an ATG translation initiation codon immediately upstream to the sequence of clone 9, and predicted an ORF commencing with this ATG and ending with a stop codon in exon 3. This ORF sequence did not correspond to that of any known gene in Genbank, nor did its putative translation share recognizable domains with or sequence similarity to any other known protein in Genbank.

Because the F04 clone was identified from our retina-specific library, these data combined indicated that the ORF corresponding to F04 represents a novel, previously unrecognized, retina expressed gene. The presence of binding sites for the CRX photoreceptor-specific transcription factor, and the highly conserved structure of the region 5' to the identified start codon identified the putative exon 1 as the first coding exon of a retina-expressed gene. Based on this information a new primer set was designed to include the potential start codon and span exons 1-4:

```
                                         SEQ ID NO: 6
Forward: 5'-ccagtggcagcaggaacc-3' (5' of exon 1)-

SEQ ID NO: 7
Reverse: 5'-ccaagccagggcatgagc-3' (3' of exon 4)-
```

RT-PCR was performed on both, an 10.4 week normal animal and an 8.6 weeks prcd affected individual resulting in a 562 bp product in both animals (see below, RT-PCR exon 1-4). The only difference observed was a G to A change observed in the affected individual which consequently was identified as the prcd mutation.

To identify the 5' and 3' ends of this gene, we created a 5' RACE retina library from a 10 week old normal dog and a 8 week old affected dog. Amplification of the 5' ends was done with different specific primers located in exon 1 (CCAAGGTGCTGAGTAGGAAGAGGGTGGTG-SEQ ID NO:8). or exon 3 (AGTCCCTGGGGCCGAGCTCCGCCTGAC-SEQ ID NO:9). Amplification of the 3' ends was done using a specific primer located on exon 1 (CACCACCCTCTTCCTACTCAGCACCTTGG-SEQ ID NO:10) which is the exact complement sequence of the specific primer that is used to run the 5' RACE. Seminested PCR was done with a primer located on exon 3 (AGGGACTGGGATCAGCTGGCAGAGGCAG-SEQ ID NO:11) to verify specificity of the product.

The consensus sequence from these experiments is the clone we consider as the cDNA for the F04 gene (see Seq ID No:3) which is shown in FIG. 2. Details of the cDNA sequence are provided above.

To validate the consensus sequence predicted from the 5' and 3' RACE, two primers were used to amplify the consensus sequence from affected and non-affected retina cDNA.

```
5'- AGTGGCAGCAGGAACCTCAGG- 3'        SEQ ID NO: 29

5'- GGATTATATTAGGGATGAATGAGAAG- 3'   SEQ ID NO: 30
```

Since the results of a 5' RACE and a 3' RACE are independent results this step is necessary to prove that this transcript is present in the affected and non-affected Retina. The RT-PCR confirmed the presence of such transcript.

By the method described above, the following sequences were obtained.

Est Clone Contig:
The clones originally contained in the EST library produced the following consensus sequence from 5 clones; 1085 bp:

```
                                        SEQ ID NO: 12
GAGCAGCTGCAGCAGCTGCCACTGCCCTGTGTCACCCCAGGGTGCA

AATGCCACCACGGGGAGCACCCCGCCCATCCCGAACTGTGTGGCTG

TGCAGATGCGGGCAGGATGGTCCTGGGCACAGGCCTTGGTCCAAGA

CCAGGCAGGCGTGGTACTTGATCTGAGGTGGGCATCATGGCACAGG

AGCTGGTCCCAGGGGTGCCCGGGGACCTTTATAGAACCTCAGTCGG

GAAGAAGCCCAAGACCTTGAGCCAGAGGGAAGTAATGCTTCTTTGT

GAGCCTCAAAAGGAGGGAAATGGCCAAGGTTTACAGTAATATAATG

ACACTAATATTATTATTAATAATGGCTAATGTGTCTCAAACGCTTC

TTACGTGCTAGGCGCTGTGCCAAGTGCTTTATTTATATGCATTGTC

TCATTTATGGGCAGGAACTGTTGTCAGTCTCATTTACCCAATAAG

GAAAGTGCTTGCTCAAGGTCACCCACAGTGAGTAGTGAAGCCAGGA

CGTGTTCCCCGGCAAGGTGATGTAAAAGCCTGTGAAGGTATTGGGC

CTCGAGGACATCCTGGGAGTGTGACCTGTCCACCAGGGCACAGGGC

ATGAGAGCTGGCAACCCTCCCTGGTGATACTGCCGCTGCTCAGTCT

GCAGAAACTCATCATTCCAGGCTGGACCAGACTCTGGGCCCCGAGG

GCAGTGACCAGAGCCACCTTTCCAGGATCTGTCATGCTCCTCAGGG

AGGAAGCAGTGGCCACTGGCAGGGATGACAGATATCAAGGTTGTCA

CTCATTGCTGCTGTTGCTCTGCTGTTTCCTCCAACCAGGGGCAGAG

CCCTGGGGGTAAGGGAGGGTGGCAGCCAGCAGCCCAGCCAGAGAAG

GAGGAGCCAGAGGAGGAAGGCTTTGTTGTTTGTTTTTACAGGGGGA

CGGTGCAGGGCTTTAAGGAGGTGGCTTCAAGACCTGCTGACTTTAG

CCATAAACTGGTACCTAAGGGTGCTGGACCCTCTCTGTGGGATACA

TATGCCCCCTAGTGGGGATTAAGCCTGGAGGGTGGCTGAG: AAATT

AAAGCAAAAAAAAAAAAAAAAAAAAA-
```

Clone9:

```
Produced by RT-PCR using primers from exon 8
and the end of exon 1 (707 bp):
                                        SEQ ID NO: 13
CACCTTGGCCATGCTCTGGCGCCGCCGGTTCGCCAACCGGGTCCAAC

CGGAGCCCAGCGGAGCAGACGGGGCAGTCGTGGGCAGCAGGTCGGAG

AGAGACCTCCAGTCCTCGGGCAGAAAGGAAGAGCCTCTGAAGTAAGT

CTTCACCCGGTCAGGCGGAGCTCGGCCCCAGGGACTGGGATCAGCTG

GCAGAGGCAGTTCAAGTCCCGGCTGGCCTCTTACCCACAAAGCATGC

TGTGGTGGAAGCAGCAGCAGCAGCAAGAAGAAAAATGGGAAAAAGCA

GTCATCAAGAAGGTAGACTCCTCCCTTTGAGTCCCTGGACCTGCCTG

GCCTCCCTTTGCCCCAGACCCTGGTGGTGGGGCTCCTGAAGCAAGGC

CTGGCTGGGGCAGGCTGGAGGGCAAAGACGCTCATTGCCCTGGCTTG

GGCTCCCTTCCTCTGAGATCCTGAGGATAGTCTGAGGCAGGCCCAGA

GAGGGACTCAGGTTTCTTATGGAAGGRCTTCTCATTCATCCCTAATA

TAATCCTTGCAATGACCCCAAGACCTTGAGCCAGAGGGAAGTAATGC

TTCTTTGTGAGCCTCAAAAGGAGGGAAATGGCCNAGGNTTACAGTAA

TATAATGACACTAATATTATTATTAATAATGGCTAATGTGTCTCAAA

CGCTTCTTACGTGCTAGGCGCTGTGCCAAGTGCTTTATTTATATGCA

TT-
```

RT-PCR Exons 1-4
This sequence was created from RT-PCR to compare the ORF of affected and non-affected animals (562 bp):

```
                                        SEQ ID NO: 14
CCAGTGGCAGCAGGAACCTCAGGATGGGCAGCAGTGGCTTGTGAGAG

CCGGCAGGGCCATTTTGGCCTTTCTCCTGCAGACTCTGTCCGGGAGG

GGATGGGGCAGCTGAGCCATGTRCACCACCCTCTTCCTACTCAGCAC

CTTGGCCATGCTCTGGCGCCGCCGGTTCGCCAACCGGGTCCAACCGG

AGCCCAGCGGAGCAGACGGGGCAGTCGTGGGCAGCAGGTCGGAGAGA

GACCTCCAGTCCTCGGGCAGAAAGGAAGAGCCTCTGAAGTAAGTCTT

CACCCGGTCAGGCGGAGCTCGGCCCCAGGGACTGGGATCAGCTGGCA

GAGGCAGTTCAAGTCCCGGCTGGCCTCTTACCCACAAAGCATGCTGT

GGTGGAAGCAGCAGCAGCAGCAAGAAGAAAAATGGGAAAAAGCAGTC

ATCAAGAAGGTAGACTCCTCCCTTTGAGTCCCTGGACCTGCCTGGCC

TCCCTTTGCCCCAGACCCTGGTGGTGGGGCTCCTGAAGCAAGGCCTG

GCTGGGGCAGGCTGGAGGGCAAAGACGCTCATTGCCCTGGCTTGG-.
```

The F04 mutation is bolded and presented as a G in normal and an A in prcd affected dogs.

Splice Variants

In addition to alternative splicing observed in some of the sequences obtained throughout the cloning process of the F04 gene (described above), different splice variants were identified using RT-PCR with primers located in exons 2 and 3, and with primers located in downstream predicted exons (see below).

Clone 1:
RT-PCR was performed using a primer from exon 3 (CAGTCGTGGGCAGCAGGTCGG-SEQ ID NO:15) and one from exon 8 (AATGCATATAAATAAAGCACTTGGC-SEQ ID NO:16) producing a 316 bp product:

```
                                        SEQ ID NO: 17
CAGTCGTGGGCAGCAGGTCGGAGAGAGACCTCCAGTCCTCGGGCAGA

AAGGAAGAGCCTCTGAAGTAAGTCTTCACCCGGTCAGGCGGAGCTCG

GCCCCAGGGGTGCCCGGGGACCTTTATAGAACCTCAGTCGGGAAGAA

GCCCAAGACCTTGAGCCAGAGGGAAGTAATGCTTCTTTGTGAGCCTC

AAAAGGAGGGAAATGGCCAAGGTTTACAGTAATATAATGACACTAAT
```

ATTATTATTAATAATGGCTAATGTGTCTCAAACGCTTCTTACGTGCT

AGGCGCTGTGCCAAGTGCTTTATTTATATGCATT-.

Primers from exon 2 (GCAGCAGGTCGGAGAGAGAC-SEQ ID NO:18) and exon 5 (CTTCCCTCAGATGTGGAGT-CAG-SEQ ID NO:19) were used to amplify cDNA obtained from normal and affected retina. Three different products were obtained as shown below.

```
Product number 1:
                                            SEQ ID NO: 20
GCCACCGGGTCCACCGGAGCCCAGCGGAGCAGACGGGGCAGTCGTGG

GCAGCAGGTCGGAGAGAGACCTCCAGTCCTCGGGCAGAAAGGAAGAG

CCTCTGAAGTAAGTCTTCACCCGGTCAGGCGGAGCTCGGCCCCAGGG

ACTGGGATCAGCTGGCAGAGGCAGTTCAAGTCCCGGCTGGCCTCTTA

CCCACAAAGCATGCTGTGGTGGAAGCAGCAGCAGCAGCAAGAAGAAA

AATGGGAAAAAGCAGTCATCAAGAAGTTTCCAGGGCACTTGCCTCTC

CCCGGTCCCCAGAGCTCACCCCGTCACCAGCCACTCTGCTGCAGTTC

TCAATAAGAAATGCCAGCTGGGATCTGTGACATGTCTGCCTGCGGCT

GGAAGGAAGCATCTCTCAACCTGTCCTCTGAGCGTGTCTGCGTGCCT

GTGTGCATGCGTGCGTGTGTTCCAAAGGGGCAGTCGCATGTGGGAAG

GGAAGAAGCCTGACACTTGTTCTTGTCAATCGCTGACTGCTCAGTA

CCACGGCGGCTCTGCCATTTCTCCCTCACAGTCCTGCTCGACCCAGA

GCAGAGATCAAAGCAGATTTCCGCTTCTGCTCCCTGAGATCCAGGCG

CAGACCTGCAGGCAGCTGCTCCCCACTGTCTGGAAGCCATTCATCAT

GCAAAGCGCCTCCCCACCAAACCCCTGCCTGCACGTGCATCGTCCCC

CCACCATCACCATCCAGCCCCAGGGTGGGCAGGGAGGTCCCTGCCT

AGCTGCACACCCCCAGGCCATCAAGAGGCAGGAGATGGGGAGT-.

Product number 2:
                                            SEQ ID NO: 21
GCCACCGGGTCCACCGGAGCCCAGCGGAGCAGACGGGGCAGTCGTGG

GCAGCAGGTCGGAGAGAGACCTCCAGTCCTCGGGCAGAAAGGAAGAG

CCTCTGAAGTAAGTCTTCACCCGGTCAGGCGGAGCTCGGCCCCAGGG

ACTGGGATCAGCTGGCAGAGGCAGTTCAAGTCCCGGCTGGCCTCTTA

CCCACAAAGCATGCTGTGGTGGAAGCAGCAGCAGCAGCAAGAAGAAA

AATGGGAAAAAGCAGTCATCAAGAAGAGCTCACCCCGTCACCAGCCA

CTCTGCTGCAGTTCTCAATAAGAAATGCCAGCTGGGATCTGTGACAT

GTCTGCCTGCGGCTGGAAGGAAGCATCTCTCAACCTGTCCTCTGAGC

GTGTCTGCGTGCCTGTGTGCATGCGTGCGTGTGTTCCAAAGGGGCAG

TCGCATGTGGGAAGGGAAGAAGCCTGACACTTGTTCTTGTCAATCTG

CTGACTGCTCAGTACCACGGCGGCTCTGCCATTTCTCCCTCACAGTC

CTGCTCGACCCAGAGCAGAGATCAAAGCAGATTTCCGCTTCTGCTCC

CTGAGATCCAGGCGCAGACCTGCAGGCAGCTGCTCCCCACTGTCTGG

AAGCCATTCATCATGCAAAGCGCCTCCCCACCAAACCCCTGCCTGCA

CGTGCATCGTCCCCCCACCATCACCATCCAGCCCCAGGGTGGGCAG
```

```
GGAGGTCCCTGCCTAGCTGCACACCCCCAGGCCATCAAGAGGCAGG

AGATGGGGAGT-.

Product number 3:
                                            SEQ ID NO: 22
GCCACCGGGTCCACCGGAGCCCAGCGGAGCAGACGGGGCAGTCGTGG

GCAGCAGGTCGGAGAGAGACCTCCAGTCCTCGGGCAGAAAGGAAGAG

CCTCTGAAGTAAGTCTTCACCCGGTCAGGCGGAGCTCGGCCCCAGGG

ACTGGGATCAGCTGGCAGAGGCAGTTCAAGTCCCGGCTGGCCTCTTA

CCCACAAAGCATGCTGTGGTGGAAGCAGCAGCAGCAGCAAGAAGAAA

AATGGGAAAAAGCAGTCATCAAGAAGTCCTGCTCGACCCAGAGCAGA

GATCAAAGCAGATTTCCGCTTCTGCTCCCTGAGATCCAGGCGCAGAC

CTGCAGGCAGCTGCTCCCCACTGTCTGGAAGCCATTCATCATGCAAA

GCGCCTCCCCACCAAACCCCTGCCTGCACGTGCATCGTCCCCCCACC

ATCACCATCCAGCCCCAGGGTGGGCAGGGAGGTCCCTGCCTAGCTG

CACACCCCCAGGCCATCAAGAGGCAGGAGATGGGGAGT-.
```

RT-PCR was done on affected and non-affected retina using the following primers:

```
5'- TTAATCAGTCTGCACAAGGTCG- 3'           SEQ ID NO: 31
5'- GGGTCATTGCAAGGATTATATTAGG- 3'        SEQ ID NO: 32
```

Two splice variants were observed:

```
Product number 1:
                                            SEQ ID NO: 33
TTAATCAGTCTGCACAAGGTCGGGTTGGCTGACCCCACTAATCAGCT

TGAGCCTCCTAATCCAGTGGCAGCAGGAACCTCAGGATGGGCAGCAG

TGGCTTGTGAGAGCCGGCAGGGCCATTTTGGCCTTTCTCCTGCAGAC

TCTGTCCGGGAGGGGATGGGGCAGCTGAGCCATGTRCACCACCCTCT

TCCTACTCAGCACCTTGGCCATGCTCTGGCGCCGCCGGTTCGCCAAC

CGGGTCCAACCGTGAGAAGCTGATGGGGCCATGGGCAGGGATGGGGA

GAGAGGAGAAGCTAGGGGGTGAGGGGTGGTGCAGGGGCTGCCTGGAC

CTCCTGGGAGGCTGGAGGGCGGGAGGATTTGCAGGGAGGTCCAGAG

AGGTTTCCCATCAGAGCACGCGGGGCGGGGCTCGCAGGTGCTCCG

AGACTGGCTGGAGTCCCCGGTCCCCCAGCCCAACACGGCCAGGAGAG

GGGGTTCTGGGCCCGGGCGCTGCCCACAGCTCTTCCAGCCTCTTCCT

CCCGCCCACAGGGAGCCCAGCGGAGCAGACGGGGCAGTCGTGGGCAG

CAGGTCGGAGAGAGACCTCCAGTCCTCGGGCAGAAAGGAAGAGCCTC

TGAAGTAAGTCTTCACCCGGTCAGGCGGAGCTCGGCCCCAGGGACTG

GATCAGCTGGCAGAGGCAGTTCAAGTCCCGGCTGGCCTCTTACCCA

CAAAGCATGCTGTGGTGGAAGCAGCAGCAGCAGCAAGAAGAAAATG

GGAAAAAGCAGTCATCAAGAAGGTAGACTCCTCCCTTTGAGTCCCTG

GACCTGCCTGGCCTCCCTTTGCCCCAGACCCTGGTGGTGGGGCTCCT

GAAGCAAGGCCTGGCTGGGGCAGGCTGGAGGGCAAAGACGCTCATTG
```

-continued

```
CCCTGGCTTGGGCTCCCTTCCTCTGAGATCCTGAGGATAGTCTGAGG

CAGGCCCAGAGAGGGACTCAGGTTTCTTATGGAAGGGCTTCTCATTC

ATCCCTAATATAATCCTTGCAATGACCC-

Product number 2:
                                            SEQ ID NO: 34
TTAATCAGTCTGCACAAGGTCGGGTTGGCTGACCCCACTAATCAGCT

TGAGCCTCCTAATCCAGTGGCAGCAGGAACCTCAGGATGGGCAGCAG

TGGCTTGTGAGAGCCGGCAGGGCCATTTTGGCCTTTCTCCTGCAGAC

TCTGTCCGGAGGGGATGGGGCAGCTGAGCCATGTRCACCACCCTCT

TCCTACTCAGCACCTTGGCCATGCTCTGGCGCCGCCGGTTCGCCAAC

CGGGTCCAACCGGAGCCCAGCGGAGCAGACGGGGCAGTCGTGGGCAG

CAGGTCGGAGAGAGACCTCCAGTCCTCGGGCAGAAAGGAAGAGCCTC

TGAAGTAAGTCTTCACCCGGTCAGGCGGAGCTCGGCCCCAGGGACTG

GGATCAGCTGGCAGAGGCAGTTCAAGTCCCGGCTGGCCTCTTACCCA

ACAAGCATGCTGTGGTGGAAGCAGCAGCAGCAGCAAGAAGAAAAATG

GGAAAAAGCAGTCATCAAGAAGGTAGACTCCTCCCTTTGAGTCCCTG

GACCTGCCTGGCCTCCCTTTGCCCCAGACCCTGGTGGTGGGGCTCCT

GAAGCAAGGCCTGGCTGGGGCAGGCTGGAGGGCAAAGACGCTCATTG

CCCTGGCTTGGGCTCCCTTCCTCTGAGATCCTGAGGATAGTCTGAGG

CAGGCCAGAGAGGGACTCAGGTTTCTTATGGAAGGGCTTCTCATTCA

TCCCTAATATAATCCTTGCAATGACCC-
```

The above results indicate that there are several retinal splice variants of F04. Based on these splice variants and comparative genomic analysis, the genomic organization of F04 was characterized. However, all splice variants relevant to prcd include exons 1-4 and the shortest and most abundantly expressed such disease-relevant transcript is the cDNA identified as SEQ ID No:3.

EXAMPLE 2

Since mapping the prcd locus to canine chromosome 9 (CFA9), we have mapped the prcd disease interval at higher resolution, narrowed the identified canine genomic region in which the prcd gene is located, and tested all candidate genes within that region. Initially, we created a physical map of the region using canine BACs (Sidjanin, 2003), and identified multiple polymorphic markers within and flanking this region. Examination of genotypes of prcd-affected dogs from multiple breeds for these polymorphic markers established that within breeds the haplotype that cosegregated with the prcd mutation extended across a broad region, including the physically mapped interval (Sidjanin et al., 2003). However, comparison of these genotypes revealed that the breed specific haplotypes varied among breeds within the area initially published (Sidjanin et al., 2003), but was consistent for all breeds for a set of markers physically located within a single BAC clone (BAC #10M13; Li et al, 1999) located adjacent to the area initially published. This BAC clone contained several genes. Single nucleotide polymorphisms were identified for each of these genes, and a single haplotype was constructed which differentiated the prcd-transmitting CFA9 from that of all normal dogs tested (Table 1) in all breeds known to be affected with prcd.

TABLE 1

Linkage disequilibrium (LD) region flanking the canine prcd/F04 gene on canine chromosome 9 (CFA9). All genes in this region are located in canine BAC # 10M13. The "affected allele" for each polymorphism is that found on all examined prcd-transmitting chromosomes from dogs of multiple breeds; the "alternative allele" is that which is present, for example, in BAC # 10M13. Where polymorphism information is bolded, the Polymorphism Name indicates the position (base number) in the F04 genomic sequence (i.e. SEQ ID NO: 1). Polymorphism Location indicates the gene in the genomic sequence of which the polymorphism is located.

| Polymorphism # | Polymorphism Name | Affected allele | Alternative allele | Polymorphism Location |
|---|---|---|---|---|
| 1 |  | A | G | FLJ22341 |
| 2 | p43 | G | T | FLJ22341 |
| 3 |  | C | T | FLJ22341 |
| 4 |  | C | T | FLJ22341 |
| 5 | b712 | A | C | FLJ22341 |
| 6 | b817 | deletion | CTG | FLJ22341 |
| 7 | b1149 | T | C | FLJ22341 |
| 8 | p49 | C | T | FLJ22341 |
| 9 |  | T | G | FLJ22341 |
| 10 | SINE | no SINE | SINE | FLJ22341 |
| 11 | p48 | G | A | FLJ22341 |
| 12 |  | A | G | FLJ22341 |
| 13 |  | A | G | FLJ22341 |
| 14 |  | T | C | FLJ22341 |
| 15 |  | C | T | FLJ22341 |
| 16 | p45 | T | C | FLJ22341 |
| 17 | p41 | C | T | FLJ22341 |
| 18 |  | C | T | FLJ22341 |
| 19 | b682 | C | G | FLJ22341 |
| 20 | b937 | A | G | FLJ22341 |
| 21 | b1130 | A | G | FLJ22341 |
| 22 | b1275 | G | deletion | FLJ22341 |
| 23 | b1351 | G | A | FLJ22341 |
| 24 | p38 | T | C | CYGB |
| 25 |  | G | A | CYGB |
| 26 |  | A | G | CYGB |
| 27 | CYGB | T | C | CYGB |
| 28 | b3128 | T | C | CYGB |
| 29 | b3133 | T | C | CYGB |
| 30 | b3605 | C | G | CYGB |
| 31 | b3769 | C | G | CYGB |
| 32 | 3820-23 | deletion | TGCC | CYGB |
| 33 | p40 | A | G | CYGB |
| 34 |  | G | A | CYGB |
| 35 |  | A | G | CYGB |
| 36 | 31F5 | A | C | CYGB |
| 37 | 31F4 | A | G | CYGB |
| 38 |  | A | G |  |
| 39 | 285 | C | T | F04 |
| 40 | 851 | C | G | F04 |
| 41 | 999 | C | T | F04 |
| 42 | 1298 | A | G | F04 |
| 43 | 1633-1635 | CTT | deletion | F04 |
| 44 | 1854 | deletion | C | F04 |
| 45 | 1912 | C | G | F04 |
| 46 | 2413 | A | G | F04 |
| 47 | 2590 | T | C | F04 |
| 48 | 2601-2603 | deletion | TCC | F04 |
| 49 | 2607 | A | G | F04 |
| 50 | 2660-2666 | ATGAGAA | deletion | F04 |
| 51 | 2710 | C | T | F04 |
| 52 | 2741 | G | A | F04 |
| 53 | 2769 | C | T | F04 |
| 54 | 3119 | G | A | F04 |
| 55 | 3804 | C | T | F04 |
| 56 | 3971 | G | C | F04 |
| 57 | 4459 | G | A | F04 |
| 58 | 5244 | G | A | F04 |
| 59 | 5698 | G | T | F04 |
| 60 | 6254 | A | C | F04 |
| 61 | 6318 | deletion | G | F04 |
| 62 | 6953 | T | C | F04 |
| 63 | 7030 | T | A | F04 |
| 64 | 7183 | A | C | F04 |
| 65 | 7239 | G | A | F04 |

TABLE 1-continued

Linkage disequilibrium (LD) region flanking the canine prcd/F04 gene on canine chromosome 9 (CFA9). All genes in this region are located in canine BAC # 10M13. The "affected allele" for each polymorphism is that found on all examined prcd-transmitting chromosomes from dogs of multiple breeds; the "alternative allele" is that which is present, for example, in BAC # 10M13. Where polymorphism information is bolded, the Polymorphism Name indicates the position (base number) in the F04 genomic sequence (i.e. SEQ ID NO: 1). Polymorphism Location indicates the gene in the genomic sequence of which the polymorphism is located.

| Polymorphism # | Polymorphism Name | Affected allele | Alternative allele | Polymorphism Location |
|---|---|---|---|---|
| 66 | 7855 | A | G | F04 |
| 67 | 8230 | C | T | F04 |
| 68 | 8843 | G | deletion | F04 |
| 69 | 8977 | G | A | F04 |
| 70 | 10230 | A | G | F04 |
| 71 | 10268 | A | C | F04 |
| 72 | 10855 | A | T | F04 |
| 73 | 12175 | A | G | F04 |
| 74 | 12613 | A | G | F04 |
| 75 | 15033 | C | T | F04 |
| 76 | 15347 | G | A | F04 |
| 77 | 15359 | A | T | F04 |
| 78 | 15445 | T | C | F04 |
| 79 | 17200 | T | C | F04 |
| 80 | 17407 | deletion | C | F04 |
| 81 | 17435-17437 | GGG | deletion | F04 |
| 82 | 17672 | T | deletion | F04 |
| 83 | 17892 | A | G | F04 |
| 84 | b1409 | C | T | STHM |
| 85 | p2 | A | C | STHM |
| 86 | STHM-NaeI | A | G | STHM |
| 87 | STHM-AvaI | C | T | STHM |
| 88 | base 3526 | C | T | STHM |
| 89 | base 3655 | G | A | STHM |
| 90 | 10-299 | G | A | STHM |
| 91 | 10-597 | G | G | STHM |
| 92 | b2263 | deletion | T | STHM |
| 93 | b2411 | T | C | STHM |
| 94 | b2425 | deletion | C | STHM |
| 95 | b2748 | G | deletion | STHM |
| 96 | from RT-PCR | A | G | STHM |

For each of these genes the exons were sequenced and examined, and a disease associated sequence change (i.e. a mutation) was found in only one gene. This gene, referred to herein as F04, is located within the interval described in U.S. Pat. No. 5,804,388. Details of the canine cDNA and genomic DNA sequence for F04 have been provided above. The mutation, at nucleotide 1298 of SEQ ID NO: 1 represents a G to A transition, from normal sequence to affected. We refer to this sequence change as the "prcd mutation" in F04 gene herein and is shown as polymorphism no. 42 in the table above.

EXAMPLE 3

This example describes a PCR-based restriction enzyme digestion test developed to identify the sequence change in the F04 gene. The following primers were used:
primer 1: ccagtggcagcaggaacc-SEQ ID NO:27
primer 2: ccgacctgctgcccacgactg-SEQ ID NO:28
PCR is run under standard conditions (annealing temp 58 degree C., 1.5MgCl2) in 25 microliters, 35 cycles. The amplification product is 512 bp in size (corresponding to by 1182 to 1693 in SEQ ID NO:1. The restriction enzyme RsaI digests the amplification product bearing the A allele, but not the G allele. Conversely, ApaLI digests the G allele but not the A allele. Both digests were performed at 37° C. for 2 hours. Restriction digestion thus yields the diagnostic results shown in Table 2:

TABLE 2

| ENZYME (restriction site) | ALLELE | FRAGMENT SIZE(S) (bp) |
|---|---|---|
| RsaI (GT\|AC) | G | 512 |
|  | A | 116; 396 |
| ApaLI (G\|TGCAC) | G | 115; 397 |
|  | A | 512 |

A large population of dogs affected with prcd was examined. We have tested more than 100 affected animals from 13 different breeds or breed varieties. These include: 36 Australian cattle dogs, 2 Chinese crested, 5 English cocker spaniels, 5 Finish Laphunds, 48 Labrador retrievers, 45 miniature or toy poodles, 1 Nova Scotia duck tolling retriever, 3 Portuguese water dogs, 1 Silky Terrier, 25 American eskimos, and 14 Entlebucher mountain dogs.

An example of the identification of the G allele (normal) and the A allele (affected allele) following RsaI digestion is shown in FIG. 3A and following digestion with ApaLI is shown in FIG. 3B. For the RsaI digestion (FIG. 3A), a normal dog (GG) shows a product of 512 bp, an affected dog (AA) shows products of 396 bp and 116 bp while a carrier dog (AG) shows products of 512 bp, 396 p and 116 bp. For the ApaLI digestion (FIG. 3B), a normal dog (GG) shows products of 397 bp and 115 bp, an affected dog (AA) shows a product of 512 bp, and a carrier dog (AG) shows products of 512 bp, 397 bp and 115 bp. Thus, this method can be used for identification of normal dogs (i.e., in which both alleles of the F04 gene have G as the nucleotide at a position corresponding to nucleotide position 1298 of SEQ ID NO:1), carrier dogs (i.e., in which one allele has G and the other allele has A as the nucleotide at a position corresponding to nucleotide position 1298 of SEQ ID NO:1) and affected or predisposed dogs (i.e., dogs in which both alleles of the F04 gene have A as the nucleotide as a position corresponding to nucleotide position 1298 of SEQ ID NO:1).

EXAMPLE 4

To confirm the exclusion of the affected allele from the general dog population, we tested 1,000 animals from 67 breeds not known to have the prcd form of PRA, to establish the absence of the "A" allele. These dogs were tested by Pyrosequencing (Biotage, Charlottesville, Va.; <http://www.pyrosequencing.com/DynPage.aspx>, Fakhrai-Rad et al., 2002; Ronagi et al., 2002; Shendure et al., May 2004) as follows. The technique is based on the amplification of the target sequence with an unlabeled forward primer and a biotin labeled (5'Bio) reverse primer, which are used to isolate a single stranded DNA product. A sequencing primer is used to start a subsequent nucleotide specific primer extension and presence or absence of a nucleotide is recorded in an allele frequency dependent manner based on a luciferase reaction.

```
Forward primer:
5'TTGTGAGAGCCGGCAGG3'-           SEQ ID NO: 23

Reverse primer:
5'Bio/ATGGCCAAGGTGCTGAGTAG3'-    SEQ ID NO: 24

Sequencing primer:
5'GGGGCAGCTGAGCCA3'-             SEQ ID NO: 25
```

Figure 4:
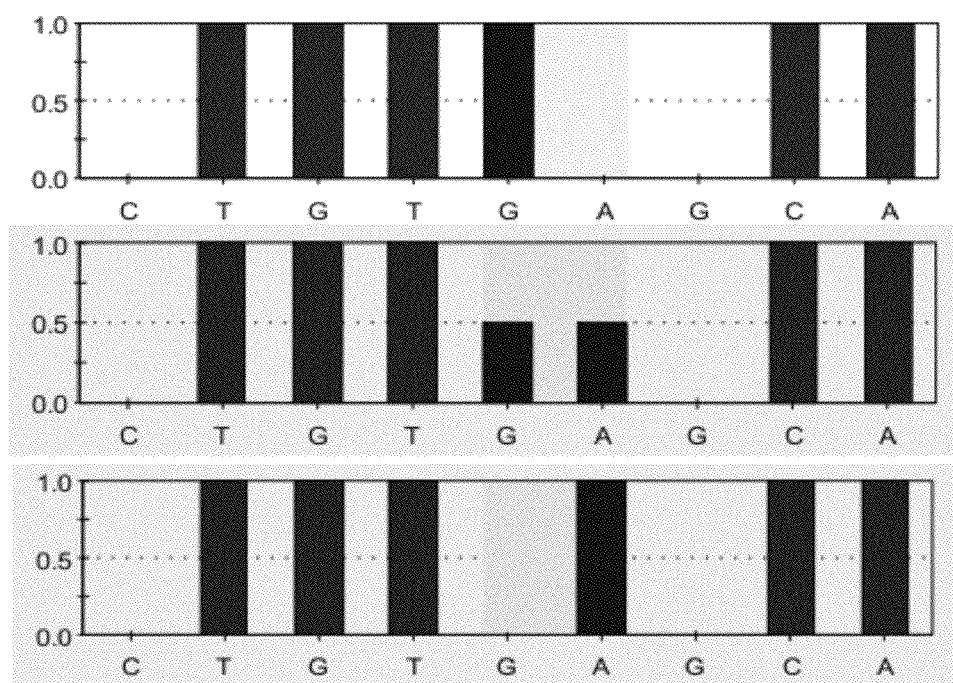
FIG. 4 is an illustration of the experimental setup used to identify whether a dog is a carrier, is affected with or is normal with respect to the prcd mutation, using Pyrosequencing™.

Product: 113 bp (primer sequence is shown in capital letter, the G/A polymorphism is bolded, and Bio indicates the biotin label: TTGTGAGAGCCGGCAGGggccattttg-gcctttctectgcagactctgtccgggagggatGGGGCA GCTGAGC- CAtgtg/acaccaccctcttcCTACTCAGCACCTTGGCCAT-Bio-SEQ ID NO:26 FIG. 4 illustrates the test set-up for the procedures of this example. Based on the test sequence, a series of nucleotides is injected one at the time during the primer extension (the sequence is shown on the bottom of each panel) and the resulting light reaction is registered (indicated by the bar for each nucleotide, directly proportional to the amount of alleles present). Nucleotides one (C) and 7 (G) of the sequence are negative controls and should not produce any light reaction. Positions 2, 3, 4, 8 and 9 are positive controls and react the same in all samples based on the tested sequence. The mutation in question corresponds to nucleotides 5 and 6. In normal animals, only the G allele is present and produces a reaction of the same strength as the positive controls. In affected individuals the same is true for the A allele, while carriers have both alleles at a 50/50 ratio and, therefore, produce half the intensity at each position. In all cases, the animals tested by Pyrosequencing™ were "GG", i.e., they had G in both alleles of the F04 gene at a position corresponding to position 1298 of SEQ ID NO:1.

It will be appreciated by those skilled in the art that routine modifications can be made to the various embodiments described above. Such modifications are intended to be within the scope of the present invention.

REFERENCES

1. Aguirre, G. D.: Inherited Retinal Degenerations in the Dog Trans. Amer. Acad. Ophth. and Otol. 81: 667, 1976.
2. Aguirre G D, Acland G M. Variation in Retinal Degeneration Phenotype Inherited at the prcd Locus. Exp. Eye Res. 46: 663, 1988
3. Acland G, Fletcher R T, Gentleman S, Chader, G. and Aguirre, G: Non-allelism of Three Genes (rcd1, rcd2 and erd) for Early-Onset Hereditary Retinal Degeneration. Exp. Eye Res. 49: 983, 1989.
4. Aguirre, G. and Acland, G.: Inherited Retinal Degeneration in the Labrador Retriever Dog. A New Animal Model of RP? Invest. Opthalmol. V is Sci. (Supp). 32(4), 1991;
5. Acland, G., Ray, K., Mellersh, C., Gu, W., Langston, A., Rine, J., Ostrander, E., and Aguirre, G. Linkage analysis and comparative mapping of canine progressive rod-cone degeneration (prcd) establishes potential locus homology with retinitis pigmentosa (RP17) in humans. Proc. Natl. Acad. Sci. USA. 95:3048-3053, 1998.
6. Fakhrai-Rad, H., Pourmand, N., Ronaghi, M. Pyrosequencing: An accurate detection platform for single nucleotide polymorphisms. Human Mutation, 2002; 19(5).
7. Kijas, J. W., Cideciyan, A. V., Aleman, T. S., Pianta, M. J., Pearce-Kelling, S. E., Miller, B. J., Jacobson, S, G., Aguirre, G. D., and Acland, G. M. Naturally-occurring rhodopsin mutation in the dog causes retinal dysfunction and degeneration mimicking human dominant retinitis pigmentosa Proc. Natl. Acad. Sciences USA 99:6328-6333, 2002.
8. Li, R., Mignot, E., Faraco, J., Kadotani, H., Cantanese, J., Zhao, B., Lin, X., Hinton, L., Ostrander, E. A., Patterson, D. F., et al. 1999. Construction and characterization of an eightfold redundant dog genomic bacterial artificial chromosome library. Genomics 58: 9-17.
9. Pearce-Kelling, S. E., Nickle, A., Kijas, J. W., Sidjanin, D. J., Miller, B. J., Aguirre, G. D. and Acland, G. M. 2002.
10. Ronagi M, Elahi E. Discovery of Single Nucleotide Polymorphisms and mutations by Pyrosequencing. Comp Funct Gemon. 2002; 3: 51-56.
11. Shendure J, Mitra R D, Varma C, Church G M. Advanced sequencing technologies: methods and goals. Nature Reviews Genetics, May 2004; 5(5), 335-344.
12. Sidjanin, D. J., Miller, B., Kijas, J. K., McElwee, J., Pillardy, J., Malek, J., Pai, G., Feldblyum, T., Fraser, C., Acland, G. and Aguirre, G. Radiation Hybrid Map, Physical Map and Low-Pass Genomic Sequence of the Canine prcd Region on CFA9, and Comparative Mapping with the Syntenic Region on Human Chromosome 17. Genomics 81:138-148, 2003.
13. Zhang, Q., Acland, G. M., Wu, W. X., Johnson, J. L. Pearce-Kelling, S., Tulloch, B., Vervoort, R., Wright, A. F., Aguirre, G. D. Different RPGR exon ORF15 Mutations in Canids Provide Insights into Photoreceptor Cell Degeneration Hum. Molec. Genet. 11:993-1003, 2002.

The invention claimed is:

1. A method for identifying a dog as genetically normal, as a carrier of, or as affected with or predisposed to progressive rod cone degeneration comprising:
   a) providing a biological sample obtained from the dog, said biological sample comprising nucleic acids; and
   b) detecting in the biological sample whether or not there is a change from G to A at position 1298 in SEQ ID NO:1, identifying the dog to be a carrier of progressive rod cone degeneration, affected with or predisposed to progressive rod cone degeneration, or normal, wherein the G to A change in one allele is indicative of a carrier of progressive rod-cone degeneration, the G to A change in both alleles is indicative of a dog affected with or predisposed to progressive rod-cone degeneration, and the absence of the G to A change is indicative of a genetically normal dog.

2. The method of claim 1, wherein the nucleic acid is DNA.

3. The method of claim 1, wherein the nucleic acid is mRNA.

4. The method of claim 1, wherein the biological sample is any tissue containing genomic DNA or mRNA.

5. The method of claim 1, wherein the biological sample is selected from the group consisting of blood, hair, mucosal scrapings, semen, tissue biopsy and saliva.

6. The method of claim 1, wherein the biological sample is saliva.

7. A method for identifying a dog as genetically normal, as a carrier of, or as affected with or predisposed to progressive rod cone degeneration comprising:
   a) providing a biological sample obtained from the dog, said biological sample comprising nucleic acids;
   b) detecting in the biological sample whether or not there is a change from G to A at position 1298 in SEQ ID NO:1;

c) based on the detecting in b), identifying the dog to be a carrier of progressive rod cone degeneration, affected with or predisposed to progressive rod cone degeneration, or normal, wherein the G to A change in one allele is indicative of a carrier of progressive rod-cone degeneration, the G to A change in both alleles is indicative of a dog affected with or predisposed to progressive rod-cone degeneration, and the absence of the G to A change is indicative of a genetically normal dog.

8. The method of claim 7, wherein the nucleic acid is DNA.

9. The method of claim 7, wherein the nucleic acid is mRNA.

10. The method of claim 7, wherein the biological sample is any tissue containing genomic DNA or mRNA.

11. The method of claim 10, wherein the biological sample is selected from the group consisting of blood, hair, mucosal scrapings, semen, tissue biopsy and saliva.

12. The method of claim 11, wherein the biological sample is saliva.

* * * * *

SEQUENCE LISTING

```
<160> NUMBER OF SEQ ID NOS: 34

<210> SEQ ID NO 1
<211> LENGTH: 18592
<212> TYPE: DNA
<213> ORGANISM: canis familiaris

<400> SEQUENCE: 1
cggccaggtg gcacctctga ctcccagccc aaacctgatg ccagtgtcca       50
cttctccctg tcgctccctc gcgacccgc ccttctcaag acttggtgtc       100
cctctgcaag tgtgagaaga ggtcggctca cctcttccgc tttggcttat      150
gtattttaaa aatcgttttt caaagtagag agcccaggtg cagccccagc      200
tctggccctc cctgggagcc tggcaggag acccctttgac accgcttcca      250 tctccttgga gggaaggaaa atctagtgca gaccyctggg gttttggag       300 agggctggag gaagctggat gctcagaccc ctgtgtgctc cacatgctgc      350
ctgggccacc tcactgaacc cctctgacag gacacccgat gcctgtgcgg      400
```

```
tgcccttcca agtggctgct cagaagcttt gcactgggaa agcaagtatt      450
cgctatttct atttagtatt tctatttagc tttatctcat cttttacaag      500
tcttatgtgt gtttattatg caggactgta ttcgcacaga tgtggaagat      550
ctaatgtatg agcagatgca tatacttatt tcatgagtgc acacttaaat      600
ccagtctttt atggaagggg ctatggaaat cagtaacatt tggggaggac      650
tgtccagagg ggagaacaca actgctcagc cgcccctcca ctcccggcc       700 tcccttgtct ttctggcttc attatctaat attcttcctc ccctcccat       750 ggctctccat gacatcattg ttctgccaac actcaacttc cagttgctgg      800
aacatgctct gtgcttttgt gtcagccgcc ccggaagagt cttctgttgg      850 sgggaggta accttccttg aacacctgca aattccaatg cccccagctc       900
ctctcccaag cattccctga cacatgcaac tccgaaagtg ctctgcgggt      950
gcctctcatc acccaagtcg ctctactgtg gtcattaatg tgacttgcya     1000
gctcaagtgt ctagactaga agccccttga gggttaggcc caggtcctag     1050
tcacatctgt atccagaatg gacagcttga tttaccctgc caccgcaggc     1100
gacaacttgg gcccagtgag gttaatcagt ctgcacaagg tcgggttggc     1150 tgacccact aatcagcttg agcctcctaa tccagtggca gcaggaacct      1200
caggatgggc agcagtggct tgtgagagcc ggcagggcca ttttggcctt     1250
tctcctgcag actctgtccg ggaggggatg gggcagctga gccatgtrca     1300
ccaccctctt cctactcagc accttggcca tgctctggcg ccgccggttc     1350
gccaaccggg tccaaccgtg agaagctgat ggggccatgg gcaggatgg      1400 ggagagagga gaagctaggg ggtgagggt ggtgcagggg ctgcctggac      1450
ctcctgggag gctggagggc ggggaggatt gcaggagg tccagagagg       1500 tttcccatca gagcacgcgg gggcggggc tcgcaggtgc tccgagactg      1550
gctggagtcc ccggtccccc agcccaacac ggccaggaga gggggttctg     1600
ggcccgggcg ctgcccacag ctcttccagc ctcttcctcc cgcccacagg     1650
gagcccagcg gagcagacgg ggcagtcgtg ggcagcaggt cggagagaga     1700
cctccagtcc tcgggcaggt aaggcagagt ctgggctggg ggaggcaggg     1750
tgcgtcgagg aagcggctgc cctggccgcc ccgaccgtgc ctgggcaggt     1800
acatgagtgc acccgagccg gcgcgccggg gcccctcgcc ccagccaccc     1850
ggtccccgtg tgcccggtgg gcagcctcgg tgtctgtgct ccccgcggc      1900 actgggcgcc csggcctgtc ctctgcaccg cagctgctct gctttgcccg     1950 agtgcgggt ggtcccccgg gtcccatcgg aaggcgcggg gggaccggag      2000 aggatgggc aggagcagct ccgggcgcc ggctcgctgc ccttccccct       2050
ccccgcggcc cccgctccgc ctcagccgct cccctgcccc ggccgccggc     2100
gggattcgcc caccggcccc caataggagg cgcaggagcg gcatgacgtc     2150
atcggcaccg cctgccattg gctgggcagc tcctgcgggc aggtcgctgt     2200
ctccagcggc cgaaagttaa ctcttcccta ggccgaagcc atgtggctcc     2250 acaaggggg aagtttgggg aacttctgga ttcttccttc cctgggtgac      2300
cagtgtcctt tgatgttagg ggctcctatg cccaacaaac cacggaaaaa     2350
tcaacatgca tttattaaga acataccgtt gtgcgtgttc ttttgtgccc     2400
```

```
ccggacccac ctrgtggggg agtcctgtgt aagggacat  tctctcctgc      2450 aaaaggtcta ctagccttct ctcaactcta gtgagacaaa gcacatgatg      2500
cccttgggct ccggggcctg tggctggagg gagtctcccc acagcgctca      2550
gatggctgag ccagtgagcg tgcctgcctg ctggggcacy ccaccggctc      2600
tcctccrggt gtgtaggacc tgcctgggtg cccctcagcc atgtggagac      2650
tggcgagcca tgagaaatga aatgggaat  ctgtctccgt atgcggcccc      2700
aaattcctcy tcggtgctgg gattcctcca agctctgaat rtcaggaggg      2750
cagccctggg catgtgccyg agacaggtat ttctgggcca cccttccttg      2800
acaatctagg ctagctgaga tggtcatgat actacccaag taggcctgct      2850
ggtgaaatgg gctgacaaag gtgaaatgat gagcactggg cctcacgcag      2900
agcaggccct tgaatgacta gtcctccctg ttgagtttgg gtctggaggc      2950
ggacagccag agtccacatc ctgactccct gcttcctgac cgagagcctc      3000
tgggaaagct atgtgatctt tctatttgta tataaactgg gattaataac      3050
agaatggtgt gggggtgttt gtgaggttca aattgagatc atcctaaagc      3100
acttggcacg aaacagctrt ttaataaatg ccggctagct attctcctgt      3150
tgttacctgg ctcttgatca gtgttctatt cttcccttga ggtctcttaa      3200
acgttaactc acttggaagt tgtaacagcc ccagagggtt ggcaagacaa      3250
gtgtttctat ctcttgttaa tggtggagga aactgaggga aggggaggcg      3300 tcagttttc  actcgaggtc atccatccta tttgtggctg atggcaactg      3350
acttcaggta gtcggtctcc tctacatgaa atgggcctgg accctccctg      3400
tcaggagaaa aagctgaat  ctggaccatc tggcccagcc tcgtggggtc      3450
tagccagaag gaagcagttg cctgttaact cccaggacc  cagttaactg      3500 gaaaaatcag cctaacatcc aacacctcct gcttcgggtg gctgttgtga      3550
agggctggtc tggggagcag taggcatgac atttctgctc tgcaattcca      3600
cagtcacaaa ttccagctga tttcctggct gctcctaccc ctcagtagtg      3650
gggtgcctcc ctaggcgtgg ggcaagggga agaagtctgg aaagacggga      3700
aggacgtccc cttcaatcct ctgactccca tgcttttctg tttagaaagg      3750
aagagcctct gaagtaagtc ttcacccggt caggcggagc tcggcccag     3800 ggaytgggat cagctggcag aggcaggtag ggcagggctg caagccttgg      3850
aaggtagagg gctgggctgg ggacaaggca ggctctgcaa ggcctggcca      3900
tgagggagca gagctccatg gagggtacac agaaggcggg tggcctctca      3950
tcagctcctg cctcaagcct sctgtggtcc aggccatggc gcaaggcttt      4000
gttagtttta agggaagggc gtggtggtgaa gtggtggtca tgctggcact      4050
gtagtgccag aggacttcta agggagaggg tgtgctctgg aatatccatt      4100
ctgcaatgca agccctgcc  ttgggatggg aggaagtgcc aatctggttt      4150
tctatttcag ttcaagtccc ggctggcctc ttacccacaa agcatgctgt      4200
ggtggaagca gcagcagcag caagaagaaa aatgggaaaa agcagtcatc      4250
aagaaggtag actcctccct ttgagtccct ggacctgcct ggcctccctt      4300
tgccccagac cctggtggtg gggctcctga agcaaggcct ggctggggca      4350
ggctggaggg caaagacgct cattgccctg gcttgggctc ccttcctctg      4400
```

```
agatcctgag gatagtctga ggcaggccca gagagggact caggtttctt        4450
atggaaggrc ttctcattca tccctaatat aatccttgca atgacccaag        4500
aagactgggc gtgttattat ccacactttt ggaaatgagg aaacagagag        4550
aggttaagga atctgtccag tgtcatccag ctagttaatc ctgcccccca        4600
ccccacccca ccccccgccc tcccagcctc ctttggaggc tgcagagccc        4650
acactcttac ccaccagggc acaggcctct ctgaaatcac ctggaagttt        4700
gcagcttgca gctgctatgt gagagcaggg gttccacggg cccggcagcc        4750
ccaaagcctg tggtccaagg ctgtgtggta tcagtttgcc atggtggcgc        4800
tctagttttcc agggcacttg cctctccccg gtccccagag ctcaccccgt       4850
caccagccac tctgctgcag ttctcaataa gaaatgccag ctgggatctg        4900
tgacatgtct gcctgcggct ggaaggaagc atctctcaac ctgtcctctg        4950
agcgtgtctg cgtgcctgtg tgcatgcgtg cgtgtgttcc aaaggggcag        5000
tcgcatgtgg gaagggaaga agcctgacac ttgttcttgt caatctgctg        5050
actgctcagt accacggcgg ctctgccatt tctccctcac agtcctgctc        5100
gacccagagc agagatcaaa gcagatttcc gcttctgctc cctgagatcc        5150
aggcgcagac ctgcaggcag ctgctcccca ctgtctggaa gccattcatc        5200
atgcaaagcg cctcccacc aaaccctgc ctgcacgtgc atcrtccccc         5250
caccatcacc atccagcccc cagggtgggc agggaggtcc ctgcctagct        5300
gcacaccccc caggccatca agaggcagga gatggggagt tctctcgaca        5350
gcagcctgtc tgccgccctg actccacatc tgagggaagg aaggaaaggg        5400
tgagatgcca cagacagagg ggaccacgct gaagccatgg gggaggggct        5450
gctgatcttg ccctggaagc ctctagaagt agggcagggt ggaggcaggg        5500
gaagggtcaa accaggggaa ggagctgtgc gctggaatgg cgacagagcc        5550
ccaccgccca ctcgacatgg gccaggagtt cgtgaccacc tgtctcagct        5600
cctgtcagcc tgtctttctc ctgcgaggtg ttggccttcc ttggtgacag        5650
ggctgtcggg ctgagggcca ggggcaccgt tcctggggcc ccatctkcg         5700
tccccgagcc cacctgtgta ttcatcctct aatctgtttg ccatgctcct        5750
gtcacttcag cctcggctct gctctctacc atttccacgt tgcctgcctc        5800
cttgcactag tctgaggaat tgtcaggcca aggtcacctg ctggacagg         5850
ggctggccca cggcccagac acacctccac gaggcgacac cccttcgctg        5900
cactgttcta gggacctgct caggagaggg tggctcctct gggcctcggt        5950
cccagaggga aggagagaag gggaagggaa gggctgctgg cgatggggg         6000
actgtgtcgg ctggccttgg cggttgcccg ggccctggca gctggggtgc        6050
catgtgggct gggcgggagg ggccctctcc cccagggagc aggctggctt        6100
cggtgggagc agattgtgtt tacaccttcc ccacacaccc agcccacgct        6150
cgcctcttat tccccgggac tctcccaccc ctgggctctc tctgcaccac        6200
gggcacgttt gcagctcctc tcctgctgca ggaagttgcc gccctcagca        6250
gagmgctcct ctacagaagg ctgccagggc ccaggcgctc cctcctcggc        6300
ccactatctc ccgtcgtggg gggggaccca gtgtccccaa gaggctgaat        6350
ccacccaccc cccattcct tggaaaacag ctgctgcttg ggaatggggg         6400
```

```
caggaaggaa agcccggggg gcttggcaga cttgaccata ataggaggga      6450
agggattaag ggcaaccaga gagagagggc cgagagagcc ggggcgcctc      6500
tggcctcagg gtgcatgaga taatgtagaa tttaagctcg gggagtccag      6550
ctccaagctc tggatttgaa tcttgactcc accatcactt tccagttctg      6600
tggcctcggg tgggttactg aatgtaaacc tgtctcagag ttgtaagggt      6650
taaattagat aatgggtata aagtgcttcg cgcacttagt aagcacgcag      6700
tatatctgag cccagggtgg ggggacagtg tttgtgagct gtcagccact      6750
gaacaactgg tcactttgca acaaccgtag gttcagaaca gctagtcctt      6800
tacctcctca ccccatggcc cttcctgccc tgtctttcca catacacaac      6850
agcagggtga tgggcagttc tggaacaaac cagagcccag cacaggggca      6900
cctggtagga cccagcaccc gggaaggctg gacgatggag caccacggtt      6950
gcytctgggt gcctggaacc ctgtccccac ctccagtggg agtcctgacc      7000
tggacatctt ccctccaact ggctctgcgw ccccaaatga atctcagctc      7050
ctagagaaga caggaggcca tggccctggt gcctttatgg tcctctgtct      7100
gaatgctaat ctctttactg gctggagcct gagtgacagg gaaaaggcgg      7150
ttctgagctg caggggtggcc gagggcggca ggmgggagca gggaggtgct      7200
gttgtctgct acttctgtgg ctgctgccag tctctcctrg agatgggaac      7250
atgaccagag agctaatgag gtggcggggg tggggtgggg ggagaaaggg      7300
aggcagacgg agcagctgca gcagctgcca ctgccctgtg tcaccccagg      7350
gtgcaaatgc caccacgggg agcacccccgc ccatcccgaa ctgtgtggct      7400
gtgcagatgc gggcaggatg gtcctgggca caggccttgg tccaagacca      7450
ggcaggcgtg gtacttgatc tgaggtgggc atcatggcac aggagctggt      7500
cccaggggtg cccggggacc tttatagaac ctcagtcggg aagaagccca      7550
agaccttgag ccagagggaa gtaatgcttc tttgtgagcc tcaaaaggag      7600
ggaaatggcc aaggtttaca gtaatataat gacactaata ttattattaa      7650
taatggctaa tgtgtctcaa acgcttctta cgtgctaggc gctgtgccaa      7700
gtgctttatt tatatgcatt gtctcattta tggggcagga actgttgtca      7750
gtctcattta cccaataagg aaagtgcttg ctcaaggtca cccacagtga      7800
gtagtgaagc caggacgtgt tccccggcaa ggtgatgtaa aagcctgtga      7850
aggtrttggg cctcgaggac atcctgggag tgtgacctgt ccaccagggc      7900
acagggcatg agagctggca acccctccctg gtgatactgc cgctgctcag      7950
tctgcagaaa ctcatcattc caggctggac cagactctgg gccccgaggg      8000
cagtgaccag agccacctttt ccaggatctg tcatgctcct cagggaggaa      8050
gcagtggcca ctgcaggga tgacagatat caaggttgtc actcattgct       8100
gctgttgctc tgctgtttcc tccaaccagg ggcagagccc tggggtaag      8150
ggagggtggc agccagcagc ccagccagag aaggaggagc cagaggagga      8200
aggctttgtt gtttgttttt acaggggay ggtgcagggc tttaaggagg       8250
tggcttcaag acctgctgac tttagccata aactggtacc taagggtgct      8300
ggaccctctc tgtgggatac atatgccccc tagtggggat taagcctgga     8350
gggtggctga gaaaattaaa gcaaaacaaa acaaaaaaag atttactgat      8400
```

| | |
|---|---|
| aggctatatg acctccgaac ctggatagga agggccaggg ctggcccct | 8450 |
| gtgtccccga gattgcacaa gcacgcacag gtttaagaca atttgcagaa | 8500 |
| cccaggtgaa cgaagcattg aaagaaatta tttaatttat tccttggtca | 8550 |
| tttatttaag aagcatgtat cgggagcctg tgatgtacac accctgtggt | 8600 |
| aggtgttgga gtcagacagc aatcaaaggg acggcgcccg atgtgccaat | 8650 |
| gaggacgaca gaaagatcct ggccgaggag gccagttgtg caagctcagc | 8700 |
| cgctgcctgc cacgactttt acttctctgg acctcagtct ccccatgtaa | 8750 |
| taggcagtgt tgaacctaag tgggctggtg cagaggatgg gaaggaccac | 8800 |
| tgactaccct ggtaaaatga aggggatgga cttcttgacc tcggggggg | 8850 |
| cccttccaga ttcaagacag gctacagtgg acagtgtttg gaggtgctga | 8900 |
| caacggtgac tcgcccactc agcaagcgtg tatggagctc ctgtatgcca | 8950 |
| ggcattgtgg gtgcagaaa tgaagcrccc agaaaactgg acaaaactga | 9000 |
| agaagcaaca gacacttgac tacaaggaac atccaagatg gtgatcccgt | 9050 |
| gaccacctca gcatctacct cccacaggtc cctgcctgag cacagggagg | 9100 |
| ggaaacccag aggactgcag tggtcttgtt cagctgagga gacaagatca | 9150 |
| gagctcagaa cagtgtgctg ttcctaaaga tatacacaca catcaatggc | 9200 |
| atctccaaaa cagacacaac gaagatgatc caatggagaa agaaaagccc | 9250 |
| ttttgaggaa acacaaaaag tgctaaccat aaaagaaaaa aacagataaa | 9300 |
| ttggacttga tcaaaattct tggaaagact ggaagagaat actagccaag | 9350 |
| caaaaatccg aacaagggcc tgtatccaaa atatataaag aacttttaca | 9400 |
| actcaataag aagacgacag cccaacggaa aagtggggga gggttttaat | 9450 |
| agacacttcg caagaaacta gacatatggc caataaacac ataaaaagat | 9500 |
| acacaacatc ctaagccatc aaggaaatgc aaattaaaac cacaatgaga | 9550 |
| tactactgca cactcaccag aatggataaa agatggacca taatagacgt | 9600 |
| gggtgaaggt gtggagcaac ttgtaaccct gtcatacgtt gctgggaaac | 9650 |
| ctgtttggca gtttcttagg atgtaatcca agaggagtga acatgtaggt | 9700 |
| ccacacaaag atttgtacag agatgttcac agcagtgtta ttatcaataa | 9750 |
| ttagtatcca aactggaaac aacgcagata gccatcaaga ggtaaatgga | 9800 |
| taaaaaaaaa aaaaaaaaaa aggaggcggt gtattcatac aatggaatac | 9850 |
| gattcagcaa taaaaggca ttgagctact atgtgagcca taacacaggg | 9900 |
| caatgagaga agccagatgc taaagagcac ctacagtatg aatccattta | 9950 |
| taggagattc tagaacaggc aataactaat cgggagtggc agaaagcaga | 10000 |
| tcagtggttg cccggggcca gggctggata tggacactgt gaaatagcag | 10050 |
| gttggtaccc tccaggggga tggagatgtt ctaaattgag actggggttg | 10100 |
| tggttttatg ggtgtatcac tggctggact attttaaatg gatgcacttt | 10150 |
| gttatatgta aattataacct caataaagat gacttaaaga gttaaaaaaa | 10200 |
| aaaaaaaaa aaagaaccac gagaatgaar acctgatcct tgtcttgctt | 10250 |
| acagtctagt gaaaacgmca gatgtgaaaa caaacaacca taaggcggtg | 10300 |
| agtagcctaa gaagcatgct caaataacaa gagttctgtt tatgaagggc | 10350 |
| tccctcgcgc cagacccaca gaggtggctt ggcgtcactg ttctagaagt | 10400 |

-continued

```
ccagataaga aaagaggctg agatggaggg gaagttgttc acgcaggatt        10450
actcagctag aatcagcagg cctgggactg ggctccaagg ctgcctgggt        10500
tcagagcagg tgccacagca gcctgtggca ggacaccgag cagagagctc        10550
gggactgttg cagcttctca ggtgagactt tgcggaggag gtattgacac        10600
aggagttgga atttgctcag cagagtagag gatgcgggga aggaaatttc        10650
aaagcaaagg gaacaaacaa tatgagcaaa ggctgggcaa cacttgtgag        10700
aaggcagggt tcctgggaat ggagagacgt gtcccgaaaa gagcagaaga        10750
ggtcaacagg atattacatg ttcttcgcat tcacttattt ttttaagaac        10800
ctattaagca ataatttta cgagaggcaa cagctctgca gggcaggcaa         10850
gtgawgtatg tgctcttggc aaacgcaggg aagaacccac cgtgatgcca        10900
aggttgcctc tttagggaaa ggggttctcc ctgtgacatt tctcctcctc        10950
caggaggtta aggctgtgtt ccaggatccc aggtttctgc tgaacaccct        11000
ttgtggcact ctttcacggt cctgagaaat cccaggagga aaaaaaaaa        11050
aacaaaaacc cgcctgtgct tttatgctgg gctttctggc tggaggaagt        11100
caagtcactg gagcgaagca aaatgtgtca cactgtcatg gtgcgttctt        11150
ctggaaactc agcacagcag tgaggtttgg aggctttgag gctggactgg        11200
ctgaggtcag atctcagcgc tcttttcacac tgattacttt ccccttttctg       11250
cactttggct tctttagaag attgcaaaag aggggtgatc ataagagggc        11300
agatgtgaga atgaagggac agtacgtgca atgtgctcag tcagactcat        11350
cgagtctgag acgttaattt agcctgtata gccttttgta tgacagtcag        11400
tcctccataa atcagttttt taaaagaag gtgcttagag cagagcctgg         11450
cccagagcaa acatttaata gacagtagct tttgtgtttt caaaaaggtg        11500
acatgcacat gtcatcccctt ttattttgct gtgacccgtt ctttcagaga       11550
attataatga gcgggattt gggacatgtt gatcatatca tttaggatga         11600
ttgtgactct taacagaaca cccaacttag ggtggctcaa acaggaagga        11650
gatttctaaa tctcacattc tggggcgcct gggtggcaca gttggttaaa        11700
cattcgactc ttggttttgg ctcaggtcat gatctcaggg ttgtgagatg        11750
gggccctgtg ttggagtctg cgctcagctc acaattctct ctctcctcca        11800
cttctgcccc tcctgccctc tctaaaataa acatttgagg gttttttaa         11850
aaagatttta tttagttagt tgagagagag acagacagag acagagagac        11900
agagagtgag catgtgtgag cacaggtggg aagggcaga gggagcagca         11950
gaatccctgc tgagcaggaa gcccaacaca gggcttgatc ccaggaccaa        12000
gatcaagacc cgagccaaag gcagatgctc atccaactga gccagccagg        12050
caaccctaaa ataaatgtct tttttaaaa aatcatcctg tgtttcactg         12100
aaactaacat gccattgctt gtgagatgcc ccttgcattc agaaatatta        12150
aaatataaaa atgtgtgtct ttgarttgaa acaaaaggtc tgaaggtagg        12200
gggctctagg actggtaatt tggcagttca ccatggagac tctttgtcct        12250
ttgtttccac tctgccatcg tcagaccttta ggctctggct ttgaggcaag       12300
cctcatggat gcaagatggc tgccagggcc tcaagcatca agtcttcaga        12350
gcctcccaaa gccagaagag aggctgctgt ttttaaaaac aagaaaaact        12400
```

```
ttcccaaact ttgcttaatt gcatcacaaa cccttttctg aattcctggc      12450
agaaggaata gatttatcat aagggtctgg tgccgactct tcaagattcg      12500
cccttagggc cggggaggag cttgcctcca ctgaagcacc gagctccagt      12550
tctgttgtga gatggaggaa gaacagctgt gagctggcaa tgagcagcgc      12600
tgccatacag atraaccgcc tgtgaatcac cggtcaactg tgcccgacag      12650
aagcagctga ctgcttggga tattcctacc caccttcctg ttcctatcaa      12700
caatggtaga gcttcctctc caggttaaga aattaacctc catattccaa      12750
agacttggtt tcctattaat gtggctttcg ggtaccgtat ccaaaatcct      12800
atccggatgg aacccagtga gttagccacc tgagcacagc aggccaatgg      12850
actagatttc acctccgtgc tcagagccaa ggcccctga ccgcaccgag        12900 gactgtggcc ttgctcagcc tgggatctac ttctgtcact gaccactaga      12950
ttgggggact ccgtgtcagt gaatacagat ccatgctagc ctaggatgac      13000
ggctacgtaa caattccact gcacataaaa actcaagtgt cccagacctc      13050
ggggcgcctg gctggcttag ggaggactga ctcttaatct cagagtcttg      13100
agttcaagcc ctgtgttggg tgtggagcct acttaaaaaa aaaaagaaga      13150
agaagaagaa ggagaaggag aaggagaagg agaaggagaa ggagaaggag      13200
aaggagaaga agaagaagaa gaagaagaag aagaagaaga agaagaagaa      13250
gaaagaagaa gaagaagaag aagaagaatt agaaatcaca acattgatgc      13300
tttgatctcc acagctctga actccgcct gctccttcag aaatctgatg        13350
cgttctctgt tgtcttcca ctgattttt tcttttttt ttaagatttt         13400 atttatttga cacacagaga gatcagcagg gggagcatca gagggagagg      13450
gagcagcagg ctccccgctg agcaggaagt ccaacatggg gctcaatccc      13500
aggaccctgg gatcatgacc tcagccaaag gcagatgttt aacccactga      13550
gccacccagg tggccctgat ttttttttta agattattta tttattttag      13600
ggatccctgg gtgcgcagc ggtttaccgc ctgccttttgg cccagggcgc       13650 aatcctggag acctgggatc gagtgccaca tcgggctccc ggtgcatggg      13700
gcctgcttct ccctctgcct atgtttctgc ctctctctct ctctctgtgt      13750
gactacaata aattaaaaaa tatttttaa tattatttat ttattttaaa       13800
atattttatt tatttattca tgagagacac agagagagag gcagagatac      13850
aggcagaggg agaagtaggc tcccacagga cttgatccca ggaccccagg      13900
atcacgacct gaatccaagg cagatgctca accactgagc cacccaggtg      13950
tcccattaaa gattatttat ttgacagaga gagagagagc aggagcagag      14000
gggcacaggg agaagaagac ttcctgctga tcgaggagcc cgacatgggg      14050
cttgaaccta gaaccctaag atcatgaccc aagttgaagg cagatgctta      14100
accaatggag ccaccaggtg ccccatcctc ccctatttct ggactgccca      14150
ggcagtgtgc cctctgcctg ccactcttcc tgcttgtgtg ctctattttt      14200
caaataaata aattaattaa aaaataataa tcttgaggca cctgggtggc      14250
tcagtggttg aacatctgtc tttggctcag ggcgtgatcc tggggtcctg      14300
ggatcgagtc ccacattggg ctccctggat ggagactgct tctctctctg      14350
cctgtgtctc tgcctctctc tctctgtgtg tgtgtgtctc tcatgaataa      14400
```

| | |
|---|---|
| ataaataaaa gggatccctg ggtggcacag tggtttagcg cctgcctttg | 14450 |
| gcccagggcg cgatcctgga gacctgggat cgaatcccac gtcgggctcc | 14500 |
| cggtgcatgg agcctgcttc tccctctgcc tatgtctggg atccctgggt | 14550 |
| ggcacagcgg tttggtgcct gcctttgggc cagggcgtga tcctggagac | 14600 |
| ccgggatcga atcccacatc gggctcccgg tgcatggagc ctgcttctcc | 14650 |
| ttctgcctgt gtctgcctct ctctctctct ctgtgtgact atcatgaata | 14700 |
| aataaataaa atcttaaaaa aaaaataaat aaataaaatc ttttttattag | 14750 |
| atttttattta aatctttttta ttagatttta atctcactgc gttttgctcc | 14800 |
| ggcctctcgg cgcctgccca gccacccgag acatgccacc tgcggtgaac | 14850 |
| ctgctgctct tctactaggt gtcctgtcag gtgtgaaagc tccactgtag | 14900 |
| accgtggcat tgtggctcct ctcaagccca gaagaatgct ccatgctcct | 14950 |
| cacacgcact agctggcaac cggtctggga ctcaagacag ccctgctaga | 15000 |
| gcccagagcc ccccagtctt gcagccatca gcycctgcag cctctcctcc | 15050 |
| tcactctgct tgccataaag tggctcaaaa ccacggaaca ggtgcccatc | 15100 |
| attccctga gtaatttcat cccaaccacc cctgcaaaca cacaaaaccc | 15150 |
| ttctttgctc ctctccccca tgcccaaaag ccctatagta agactgatgt | 15200 |
| atagatatac gaagttcagt acatcttagt ggtgagagta tggactctgc | 15250 |
| aggctggcct caaaccttga ccccagcaat cactagttgt gtgaatttgg | 15300 |
| gaaagtcacc tcatctctca ctcacctcac ctcatctgcg aaatgcrggt | 15350 |
| agtgatagwg cccttcagag ggcagcggtg cacattaaac aaattggtgt | 15400 |
| gcgttcagta ctccaggagt ggacggcgca tggtaagtgc taccyggtat | 15450 |
| ccactctcgc tgttattcgg cctgcagcgg gtcccttgcc tccatccaag | 15500 |
| cagctctggg gaacttccac attcaaaact ccctctccga gtctgaaaat | 15550 |
| gaaaggaact tagttttcag ggagagagcc cattcctcct ttccctattc | 15600 |
| tacaaaactg tattcaaggg caagacagaa atgcaagggc cagtttcata | 15650 |
| agacagatgt tactgccaag tgagtcaatg attatctgtt gtgtacgtgg | 15700 |
| gcagaggcag aggaataaca accagactct gggaggcaat taaaaagaaa | 15750 |
| aaaaaaaaa gtaaaagagt gtctcatgga gcgcctgggt ggctcagtcc | 15800 |
| gttaagcctt ggacttttgg tttcccctca ggtcatgatc tcagggtcgt | 15850 |
| gggacccagc cctggggcgg gctctgtgat cagtggggag cctgcttgag | 15900 |
| attccctcct tctgctgtgc acactctctc tctaaaataa atacgtcttt | 15950 |
| agaagagcaa gcgagcgaga gatgcttccc gcctagaaga gcttacaatc | 16000 |
| aaatcaaggg aggcaaacat aaacaagtgt ggcaacttga taataagcac | 16050 |
| ctgcgaccta tggccataca cagaataaca taacccagac taaatgccac | 16100 |
| tgcatagtca ctagcgggtt gatgacaacg ggggaggct aatgctgaaa | 16150 |
| aggcctttct gtcttataag tttaaactaa tttctggggg cacctgggtg | 16200 |
| gctctggttg agcatctgcc tttggtcgt cgtcccaggg tcctgagatc | 16250 |
| gagtccctca tccggctccc agccccgtag gagcctgctt ctccctctgc | 16300 |
| ctcttcctct ctgtctctca tgaataaata aataaaaatt ttaagggatg | 16350 |
| cccgggtggc tcagcggttt agcgcctgcc tttggcccag ggtgtgatcc | 16400 |

```
tggggtcccg agatcgagtc ccacatcgag tcccacatcg agttccggga        16450
tcgagtccct gcagggaacc tgcttctccc tctccctgtg tgtgtgtctc        16500
tctctctttc tgtatctctc atgaataaat aagaaaatc tttaaaaata         16550
aataaataaa aacagtattt aaaaaaatga actaatttcc aagtaggtgt        16600
aaattctggc tcggactagt gaatggctct ggctctgctg catcacccac        16650
cgccagggct ctgggccgct ccgagcccg ctcgccggcg ccccctgccg         16700
cccgggcctc ccgccttcac cccaacccgc agggcggcgg agccctaggc        16750
ccaatcggcc ccgggaacct gccgcctctt ctctagcgca acccagcacc        16800
cagatgaccc cttttccgcc ccaggtgcag tccggccggg ccctggtgtc        16850
ctcacccgtt cccctaggga gacccctctc gaaccttctg cgccacccta       16900
ctctacgcca gggaaaatct gtgcactcag tagataaatg cttgtaactg        16950
aagcaaccgt ctccgtggct ccagaatcgc gctgaggatg ctgctgccgc        17000
accccacct cccccggctc cggcggaggt tgtttggact acacttccca         17050
tgaggcccct ctcaacatcg cgataactct cgcgagaccg ctgggaagag        17100
ttgtgcgcag gcgcagcccc gccttcttgt cgaggcaggc cgcgtggccg        17150
gcagtcatgg cggctccttg ctggcccgac cgggacaggg agtctggagy        17200
ctctggctgt ggtaaggttg tcgaggcggg cagacgggat cgtccttggc        17250
ccggcgctag ttcgctcggc ctccctttcc tcggggcgg gatgatgacg         17300
gtaaagccgg tcttcctcgt agggtggttg ggttagttga gatgctggat        17350
cggaaaacgc tttctgagcg gcgcgagtgt tgacgatcga agggagagag        17400
ctcaggcccc ccttggagtc agagggcccc tcctgggggg ggggtcctc         17450
cagcctgtgc agccccgtgt gtgccctgcg ggtctcccgg gccgcccac         17500
gggaggctgc cggtggtagt tcttaatcca catcaagtgt taacgtgagg        17550
gtcctggagt gccccgaggt cggccctggt cagtggttcg tattcagtcc        17600
tacagatagt agtaaagggg cttgtagatt ttggaaagcc ataatgctct        17650
gcgccctacc ttccatgttc atttttttc ccctctctct tcccgtacag         17700
ggttttcttt gcgtcgcaga cctgcaggtt gaagcttaaa agtagcgaat        17750
ggggagccct gtgaaatggg taaggatggg tgctggcagg gcccgggtgg        17800
tgaccagaag tgagaaagtc gagatggtgg gcaggcctgc cacacccggc       17850
cgccgcacgc tttactttac taattttatt ttttttttaaa grtttaatta      17900
attaattaat taatgatagg cagagacaca ggcagaggga gaagcaggct       17950
ccgtgccggg agcccgacgc gggactccag gatcgcgccc tgggccaaag       18000
gcaggcgcca aaccgctgag ccacccaggg atcccacttt accgatttta       18050
agttcggttc ttaggaacac gtggacgcac gcatccggtt agggtgagaa       18100
gaaaacggac ccgggtcctg gaagcgagca gggccttgcc agtgtgactc       18150
ggcgccgcta ggtgtcactg tttggattca aaccggttgc cgcgcacgag       18200
gttggcgggg aggcttagga aatgggcttc ggtggggttt ggaagtattt       18250
gtggatgatt taaagttatc tttgtcttaa agggctcttt tgtgaagagt       18300
tttgatgcgt tgaggctcag cttttttttt tttttttttt taaggtttgt      18350
attcattttt tcacagagag gcagagggag gagaagcttg ctgcctgcag       18400
```

```
agagcaggat gcgagactcg atccctggat ttcgggatca cgcccagagc        18450
caaaggcaga cacgcaacta ctgagccacc caggcgtccc gaggcccag         18500 cttcttaaat aaccaatctt gagaataaca tcttgacctc atttctctta        18550
gaatatactt tgttacattt cccttagaga ttaaaggtgt tg                18592
```

<210> SEQ ID NO 2
<211> LENGTH: 54
<212> TYPE: PRT
<213> ORGANISM: canis familiaris

<400> SEQUENCE: 2

Met Cys Thr Thr Leu Phe Leu Leu Ser Thr Leu Ala
            5                   10
Met Leu Trp Arg Arg Arg Phe Ala Asn Arg Val Gln
        15                  20
Pro Glu Pro Ser Gly Ala Asp Gly Ala Val Val Gly
    25                  30                  35
Ser Arg Ser Glu Arg Asp Leu Gln Ser Ser Gly Arg
            40                  45
Lys Glu Glu Pro Leu Lys
        50

<210> SEQ ID NO 3
<211> LENGTH: 695
<212> TYPE: DNA
<213> ORGANISM: canis familiaris

<400> SEQUENCE: 3

```
agtggcagca ggaacctcag gatgggcagc agtggcttgt gagagccggc        50
agggccattt tggcctttct cctgcagact ctgtccggga ggggatgggg       100
cagctgagcc atgtrcacca ccctcttcct actcagcacc ttggccatgc       150 tctgcgccg ccggttcgcc aaccgggtcc aaccggagcc cagcggagca        200
gacggggcag tcgtgggcag caggtcggag agagacctcc agtcctcggg       250
cagaaaggaa gagcctctga agtaagtctt caccggtca ggcggagctc        300 ggccccaggg aytgggatca gctggcgagg gcagttcaag tcccggctgg       350
cctcttaccc acaaagcatg ctgtggtgga agcagcagca gcagcaagaa       400
gaaaaatggg aaaagcagt catcaagaag gtagactcct cccttttgagt       450 ccctggacct gcctggcctc cctttgcccc agaccctggt ggtggggctc       500
ctgaagcaag gcctggctgg ggcaggctgg agggcaaaga cgctcattgc       550
cctggcttgg gctcccttcc tctgagatcc tgaggatagt ctgaggcagg       600
cccagagagg gactcaggtt tcttatggaa ggrcttctca ttcatcccta       650
atataatcct tgcaatgacc caaaaaaaaa aaaaaaaaaa aaaaa             695
```

<210> SEQ ID NO 4
<211> LENGTH: 20
<212> TYPE: DNA
<213> ORGANISM: artificial sequence
<220> FEATURE:
<223> OTHER INFORMATION: RT-PCR forward primer

<400> SEQUENCE: 4

```
cacccttggcc atgctctggc                                        20
```

```
<210> SEQ ID NO 5
<211> LENGTH: 25
<212> TYPE: DNA
<213> ORGANISM: artificial sequence
<220> FEATURE:
<223> OTHER INFORMATION: RT-PCR reverse primer

<400> SEQUENCE: 5
aatgcatata aataaagcac ttggc                                    25

<210> SEQ ID NO 6
<211> LENGTH: 18
<212> TYPE: DNA
<213> ORGANISM: artificial sequence
<220> FEATURE:
<223> OTHER INFORMATION: RT-PCR forward primer

<400> SEQUENCE: 6
ccagtggcag caggaacc                                            18

<210> SEQ ID NO 7
<211> LENGTH: 18
<212> TYPE: DNA
<213> ORGANISM: artificial sequence
<220> FEATURE:
<223> OTHER INFORMATION: RT-PCR reverse primer

<400> SEQUENCE: 7
ccaagccagg gcatgagc                                            18

<210> SEQ ID NO 8
<211> LENGTH: 29
<212> TYPE: DNA
<213> ORGANISM: artificial sequence
<220> FEATURE:
<223> OTHER INFORMATION: reverse primer located on exon 1

<400> SEQUENCE: 8
ccaaggtgct gagtaggaag agggtggtg                                29

<210> SEQ ID NO 9
<211> LENGTH: 27
<212> TYPE: DNA
<213> ORGANISM: artificial sequence
<220> FEATURE:
<223> OTHER INFORMATION: reverse primer located on exon 3

<400> SEQUENCE: 9
agtccctggg gccgagctcc gcctgac                                  27

<210> SEQ ID NO 10
<211> LENGTH: 29
<212> TYPE: DNA
<213> ORGANISM: artificial sequence
<220> FEATURE:
<223> OTHER INFORMATION: forward primer located on exon 1

<400> SEQUENCE: 10
caccaccctc ttcctactca gcaccttgg                                29

<210> SEQ ID NO 11
<211> LENGTH: 28
<212> TYPE: DNA
<213> ORGANISM: artificial sequence
<220> FEATURE:
<223> OTHER INFORMATION: forward primer located on exon 3

<400> SEQUENCE: 11
```

| | |
|---|---|
| agggactggg atcagctggc agaggcag | 28 |

<210> SEQ ID NO 12
<211> LENGTH: 1084
<212> TYPE: DNA
<213> ORGANISM: artificial sequence
<220> FEATURE:
<223> OTHER INFORMATION: EST clone contig

<400> SEQUENCE: 12

| | |
|---|---|
| gagcagctgc agcagctgcc actgccctgt gtcaccccag ggtgcaaatg | 50 |
| ccaccacggg gagcaccccg cccatcccga actgtgtggc tgtgcagatg | 100 |
| cgggcaggat ggtcctgggc acaggccttg gtccaagacc aggcaggcgt | 150 |
| ggtacttgat ctgaggtggg catcatggca caggagctgg tcccaggggt | 200 |
| gcccggggac ctttatagaa cctcagtcgg gaagaagccc aagaccttga | 250 |
| gccagaggga agtaatgctt ctttgtgagc ctcaaaagga gggaaatggc | 300 |
| caaggtttac agtaatataa tgacactaat attattatta ataatggcta | 350 |
| atgtgtctca aacgcttctt acgtgctagg cgctgtgcca agtgctttat | 400 |
| ttatatgcat tgtctcattt atggggcagg aactgttgtc agtctcattt | 450 |
| acccaataag gaaagtgctt gctcaaggtc acccacagtg agtagtgaag | 500 |
| ccaggacgtg ttccccggca aggtgatgta aaagcctgtg aaggtattgg | 550 |
| gcctcgagga catcctggga gtgtgacctg tccaccaggg cacagggcat | 600 |
| gagagctggc aaccctccct ggtgatactg ccgctgctca gtctgcagaa | 650 |
| actcatcatt ccaggctgga ccagactctg ggccccgagg gcagtgacca | 700 |
| gagccacctt tccaggatct gtcatgctcc tcagggagga agcagtggcc | 750 |
| actggcaggg atgacagata tcaaggttgt cactcattgc tgctgttgct | 800 |
| ctgctgtttc ctccaaccag gggcagagcc ctgggggtaa gggagggtgg | 850 |
| cagccagcag cccagccaga gaaggaggag ccagaggagg aaggctttgt | 900 |
| tgtttgtttt tacaggggga cggtgcaggg cttttaaggag gtggcttcaa | 950 |
| gacctgctga ctttagccat aaactggtac ctaagggtgc tggaccctct | 1000 |
| ctgtgggata catatgcccc ctagtgggga ttaagcctgg agggtggctg | 1050 |
| agaaattaaa gcaaaaaaaa aaaaaaaaaa aaaa | 1084 |

<210> SEQ ID NO 13
<211> LENGTH: 707
<212> TYPE: DNA
<213> ORGANISM: artificial sequence
<220> FEATURE:
<221> NAME/KEY: unsure
<222> LOCATION: 598, 602
<223> OTHER INFORMATION: Clone 9 sequence; RT-PCR product

<400> SEQUENCE: 13

| | |
|---|---|
| caccttggcc atgctctggc gccgccggtt cgccaaccgg gtccaaccgg | 50 |
| agcccagcgg agcagacggg gcagtcgtgg gcagcaggtc ggagagagac | 100 |
| ctccagtcct cgggcagaaa ggaagagcct ctgaagtaag tcttcacccg | 150 |
| gtcaggcgga gctcggcccc agggactggg atcagctggc agaggcagtt | 200 |
| caagtcccgg ctggcctctt acccacaaag catgctgtgg tggaagcagc | 250 |
| agcagcagca agaagaaaaa tgggaaaaag cagtcatcaa gaaggtagac | 300 |

```
tcctcccttt gagtccctgg acctgcctgg cctcccttttg ccccagaccc          350 tggtggtggg gctcctgaag caaggcctgg ctggggcagg ctggagggca          400
aagacgctca ttgccctggc ttgggctccc ttcctctgag atcctgagga          450
tagtctgagg caggcccaga gagggactca ggtttcttat ggaaggrctt          500
ctcattcatc cctaatataa tccttgcaat gaccccaaga ccttgagcca          550
gagggaagta atgcttcttt gtgagcctca aaaggaggga aatggccnag          600
gnttacagta atataatgac actaatatta ttattaataa tggctaatgt          650
gtctcaaacg cttcttacgt gctaggcgct gtgccaagtg ctttatttat          700
atgcatt                                                          707

<210> SEQ ID NO 14
<211> LENGTH: 562
<212> TYPE: DNA
<213> ORGANISM: artificial sequence
<220> FEATURE:
<223> OTHER INFORMATION: RT-PCR exons 1-4

<400> SEQUENCE: 14
ccagtggcag caggaacctc aggatgggca gcagtggctt gtgagagccg           50
gcagggccat tttggccttt ctcctgcaga ctctgtccgg gaggggatgg          100
ggcagctgag ccatgtrcac caccctcttc ctactcagca ccttggccat          150
gctctggcgc cgccggttcg ccaacccggt ccaaccggag cccagcggag          200
cagacggggc agtcgtgggc agcaggtcgg agagagacct ccagtcctcg          250
ggcagaaagg aagagcctct gaagtaagtc ttcacccggt caggcggagc          300
tcggccccag ggactgggat cagctggcag aggcagttca agtcccggct          350
ggcctcttac ccacaaagca tgctgtggtg gaagcagcag cagcagcaag          400
aagaaaaatg ggaaaaagca gtcatcaaga aggtagactc ctcccttga           450 gtccctggac ctgcctggcc tccctttgcc ccagaccctg gtggtggggc          500
tcctgaagca aggcctggct ggggcaggct ggagggcaaa gacgctcatt          550
gccctggctt gg                                                    562

<210> SEQ ID NO 15
<211> LENGTH: 21
<212> TYPE: DNA
<213> ORGANISM: artificial sequence
<220> FEATURE:
<223> OTHER INFORMATION: RT-PCR forward primer from exon 3

<400> SEQUENCE: 15
cagtcgtggg cagcaggtcg g                                          21

<210> SEQ ID NO 16
<211> LENGTH: 25
<212> TYPE: DNA
<213> ORGANISM: artificial sequence
<220> FEATURE:
<223> OTHER INFORMATION: RT-PCR reverse primer from exon 8

<400> SEQUENCE: 16
aatgcatata aataaagcac ttggc                                      25

<210> SEQ ID NO 17
<211> LENGTH: 316
```

```
<212> TYPE: DNA
<213> ORGANISM: artificial sequence
<220> FEATURE:
<223> OTHER INFORMATION: RT-PCR product

<400> SEQUENCE: 17
cagtcgtggg cagcaggtcg agagagacc tccagtcctc gggcagaaag        50
gaagagcctc tgaagtaagt cttcacccgg tcaggcggag ctcggcccca      100
ggggtgcccg gggacccttta tagaacctca gtcgggaaga agcccaagac     150
cttgagccag agggaagtaa tgcttctttg tgagcctcaa aaggagggaa      200
atggccaagg tttacagtaa tataatgaca ctaatattat tattaataat     250
ggctaatgtg tctcaaacgc ttcttacgtg ctaggcgctg tgccaagtgc     300
tttatttata tgcatt                                           316

<210> SEQ ID NO 18
<211> LENGTH: 20
<212> TYPE: DNA
<213> ORGANISM: artificial sequence
<220> FEATURE:
<223> OTHER INFORMATION: RT-PCR forward primer from exon 2

<400> SEQUENCE: 18
gcagcaggtc ggagagagac                                        20

<210> SEQ ID NO 19
<211> LENGTH: 22
<212> TYPE: DNA
<213> ORGANISM: artificial sequence
<220> FEATURE:
<223> OTHER INFORMATION: RT-PCR reverse primer from exon 5

<400> SEQUENCE: 19
cttccctcag atgtggagtc ag                                     22

<210> SEQ ID NO 20
<211> LENGTH: 796
<212> TYPE: DNA
<213> ORGANISM: artificial sequence
<220> FEATURE:
<223> OTHER INFORMATION: RT-PCR product no. 1

<400> SEQUENCE: 20
gccaccgggt ccaccggagc ccagcggagc agacggggca gtcgtgggca       50
gcaggtcgga gagagacctc cagtcctcgg gcagaaagga agagcctctg      100
aagtaagtct tcacccggtc aggcggagct cggccccagg gactgggatc     150
agctggcaga ggcagttcaa gtcccggctg gcctcttacc cacaaagcat     200
gctgtggtgg aagcagcagc agcagcaaga agaaaaatgg gaaaaagcag     250
tcatcaagaa gtttccaggg cacttgcctc tccccggtcc ccagagctca     300
ccccgtcacc agccactctg ctgcagttct caataagaaa tgccagctgg     350
gatctgtgac atgtctgcct gcggctggaa ggaagcatct ctcaacctgt     400
cctctgagcg tgtctgcgtg cctgtgtgca tgcgtgcgtg tgttccaaag     450
gggcagtcgc atgtgggaag ggaagaagcc tgacacttgt tcttgtcaat     500
ctgctgactg ctcagtacca cggcggctct gccatttctc cctcacagtc     550
ctgctcgacc cagagcagag atcaaagcag atttccgctt ctgctccctg     600
agatccaggc gcagacctgc aggcagctgc tccccactgt ctggaagcca     650
```

| | |
|---|---:|
| ttcatcatgc aaagcgcctc cccaccaaac ccctgcctgc acgtgcatcg | 700 |
| tccccccacc atcaccatcc agcccccagg gtgggcaggg aggtccctgc | 750 |
| ctagctgcac acccccagg ccatcaagag gcaggagatg gggagt | 796 |

<210> SEQ ID NO 21
<211> LENGTH: 763
<212> TYPE: DNA
<213> ORGANISM: artificial sequence
<220> FEATURE:
<223> OTHER INFORMATION: RT-PCR product no. 2

<400> SEQUENCE: 21

| | |
|---|---:|
| gccaccgggt ccaccggagc ccagcggagc agacggggca gtcgtgggca | 50 |
| gcaggtcgga gagagacctc cagtcctcgg gcagaaagga agagcctctg | 100 |
| aagtaagtct tcacccggtc aggcggagct cggccccagg gactgggatc | 150 |
| agctggcaga ggcagttcaa gtcccggctg gcctcttacc cacaaagcat | 200 |
| gctgtggtgg aagcagcagc agcagcaaga agaaaaatgg gaaaaagcag | 250 |
| tcatcaagaa gagctcaccc cgtcaccagc cactctgctg cagttctcaa | 300 |
| taagaaatgc cagctgggat ctgtgacatg tctgcctgcg gctggaagga | 350 |
| agcatctctc aacctgtcct ctgagcgtgt ctgcgtgcct gtgtgcatgc | 400 |
| gtgcgtgtgt tccaaagggg cagtcgcatg tgggaaggga agaagcctga | 450 |
| cacttgttct tgtcaatctg ctgactgctc agtaccacgg cggctctgcc | 500 |
| atttctccct cacagtcctg ctcgacccag agcagagatc aaagcagatt | 550 |
| tccgcttctg ctccctgaga tccaggcgca gacctgcagg cagctgctcc | 600 |
| ccactgtctg gaagccattc atcatgcaaa gcgcctcccc accaaaccc | 650 |
| tgcctgcacg tgcatcgtcc ccccaccatc accatccagc cccagggtg | 700 |
| ggcagggagg tccctgccta gctgcacacc ccccaggcca tcaagaggca | 750 |
| ggagatgggg agt | 763 |

<210> SEQ ID NO 22
<211> LENGTH: 509
<212> TYPE: DNA
<213> ORGANISM: artificial sequence
<220> FEATURE:
<223> OTHER INFORMATION: RT-PCR product no. 3

<400> SEQUENCE: 22

| | |
|---|---:|
| gccaccgggt ccaccggagc ccagcggagc agacggggca gtcgtgggca | 50 |
| gcaggtcgga gagagacctc cagtcctcgg gcagaaagga agagcctctg | 100 |
| aagtaagtct tcacccggtc aggcggagct cggccccagg gactgggatc | 150 |
| agctggcaga ggcagttcaa gtcccggctg gcctcttacc cacaaagcat | 200 |
| gctgtggtgg aagcagcagc agcagcaaga agaaaaatgg gaaaaagcag | 250 |
| tcatcaagaa gtcctgctcg acccagagca gagatcaaag cagatttccg | 300 |
| cttctgctcc ctgagatcca ggcgcagacc tgcaggcagc tgctccccac | 350 |
| tgtctggaag ccattcatca tgcaaagcgc ctccccacca aaccctgcc | 400 |
| tgcacgtgca tcgtcccccc accatcacca tccagccccc agggtgggca | 450 |
| gggaggtccc tgcctagctg cacacccccc aggccatcaa gaggcaggag | 500 |
| atggggagt | 509 |

<210> SEQ ID NO 23
<211> LENGTH: 17
<212> TYPE: DNA
<213> ORGANISM: artificial sequence
<220> FEATURE:
<223> OTHER INFORMATION: Pyrosequencing forward primer

<400> SEQUENCE: 23
ttgtgagagc cggcagg                                                17

<210> SEQ ID NO 24
<211> LENGTH: 20
<212> TYPE: DNA
<213> ORGANISM: artificial sequence
<220> FEATURE:
<223> OTHER INFORMATION: Pyrosequencing biotin labeled reverse primer

<400> SEQUENCE: 24
atggccaagg tgctgagtag                                             20

<210> SEQ ID NO 25
<211> LENGTH: 15
<212> TYPE: DNA
<213> ORGANISM: artificial sequence
<220> FEATURE:
<223> OTHER INFORMATION: Pyrosequencing oligo probe

<400> SEQUENCE: 25
ggggcagctg agcca                                                  15

<210> SEQ ID NO 26
<211> LENGTH: 113
<212> TYPE: DNA
<213> ORGANISM: artificial sequence
<220> FEATURE:
<223> OTHER INFORMATION: Pyrosequencing PCR product

<400> SEQUENCE: 26
ttgtgagagc cggcaggggc cattttggcc tttctcctgc agactctgtc             50
cgggagggga tggggcagct gagccatgtr caccaccctc ttcctactca            100
gcaccttggc cat                                                   113

<210> SEQ ID NO 27
<211> LENGTH: 18
<212> TYPE: DNA
<213> ORGANISM: artificial sequence
<220> FEATURE:
<223> OTHER INFORMATION: forward primer

<400> SEQUENCE: 27
ccagtggcag caggaacc                                               18

<210> SEQ ID NO 28
<211> LENGTH: 21
<212> TYPE: DNA
<213> ORGANISM: primer 2
<220> FEATURE:
<223> OTHER INFORMATION: reverse primer

<400> SEQUENCE: 28
ccgacctgct gcccacgact g                                           21

<210> SEQ ID NO 29
<211> LENGTH: 21

```
<212> TYPE: DNA
<213> ORGANISM: artificial sequence
<220> FEATURE:
<223> OTHER INFORMATION: RT-PCR forward primer

<400> SEQUENCE: 29
agtggcagca ggaacctcag g                                                   21

<210> SEQ ID NO 30
<211> LENGTH: 26
<212> TYPE: DNA
<213> ORGANISM: artificial sequence
<220> FEATURE:
<223> OTHER INFORMATION: RT-PCR reverse primer

<400> SEQUENCE: 30
ggattatatt agggatgaat gagaag                                              26

<210> SEQ ID NO 31
<211> LENGTH: 22
<212> TYPE: DNA
<213> ORGANISM: artificial sequence
<220> FEATURE:
<223> OTHER INFORMATION: RT-PCR forward primer

<400> SEQUENCE: 31
ttaatcagtc tgcacaaggt cg                                                  22

<210> SEQ ID NO 32
<211> LENGTH: 25
<212> TYPE: DNA
<213> ORGANISM: RT-PCR reverse primer
<220> FEATURE:
<223> OTHER INFORMATION: amplification primer

<400> SEQUENCE: 32
gggtcattgc aaggattata ttagg                                               25

<210> SEQ ID NO 33
<211> LENGTH: 1015
<212> TYPE: DNA
<213> ORGANISM: artificial sequence
<220> FEATURE:
<223> OTHER INFORMATION: RT-PCR splice variant product no. 1

<400> SEQUENCE: 33
ttaatcagtc tgcacaaggt cgggttggct gaccccacta atcagcttga         50
gcctcctaat ccagtggcag caggaacctc aggatgggca gcagtggctt        100
gtgagagccg gcagggccat tttggccttt ctcctgcaga ctctgtccgg        150
gaggggatgg ggcagctgag ccatgtrcac caccctcttc ctactcagca        200
ccttggccat gctctggcgc cgccggttcg ccaaccgggt ccaaccgtga        250
gaagctgatg gggccatggg cagggatggg gagagaggag aagctagggg        300
gtgaggggtg gtgcaggggc tgcctggacc tcctgggagg ctggagggcg        350
gggaggattt gcagggaggt ccagagaggt ttcccatcag agcacgcggg        400
ggcgggggct cgcaggtgct ccgagactgg ctggagtccc cggtcccca         450
gcccaacacg gccaggagag ggggttctgg gcccgggcgc tgcccacagc        500
tcttccagcc tcttcctccc gcccacaggg agcccagcgg agcagacggg        550
gcagtcgtgg gcagcaggtc ggagagagac ctccagtcct cgggcagaaa        600
ggaagagcct ctgaagtaag tcttcacccg gtcaggcgga gctcggcccc        650
```

```
agggactggg atcagctggc agaggcagtt caagtcccgg ctggcctctt          700
acccacaaag catgctgtgg tggaagcagc agcagcagca agaagaaaaa          750
tgggaaaaag cagtcatcaa gaaggtagac tcctcccttt gagtccctgg          800
acctgcctgg cctcccttttg ccccagaccc tggtggtggg gctcctgaag         850
caaggcctgg ctggggcagg ctggagggca aagacgctca ttgccctggc          900
ttgggctccc ttcctctgag atcctgagga tagtctgagg caggcccaga          950
gagggactca ggtttcttat ggaagggctt ctcattcatc cctaatataa         1000
tccttgcaat gaccc                                               1015

<210> SEQ ID NO 34
<211> LENGTH: 733
<212> TYPE: DNA
<213> ORGANISM: artificial sequence
<220> FEATURE:
<223> OTHER INFORMATION: RT-PCR splice variant product no. 2

<400> SEQUENCE: 34
ttaatcagtc tgcacaaggt cgggttggct gaccccacta atcagcttga           50
gcctcctaat ccagtggcag caggaacctc aggatgggca gcagtggctt          100
gtgagagccg gcagggccat tttggccttt ctcctgcaga ctctgtccgg          150
gaggggatgg ggcagctgag ccatgtrcac caccctcttc ctactcagca          200
ccttggccat gctctggcgc cgccggttcg ccaaccgggt ccaaccggag          250
cccagcggag cagacggggc agtcgtgggc agcaggtcgg agagagacct          300
ccagtcctcg ggcagaaagg aagagcctct gaagtaagtc ttcacccggt          350
caggcggagc tcggccccag ggactgggat cagctggcag aggcagttca          400
agtcccggct ggcctcttac ccacaaagca tgctgtggtg gaagcagcag          450
cagcagcaag aagaaaaatg ggaaaaagca gtcatcaaga aggtagactc          500
ctccctttga gtccctggac ctgcctggcc tcccttttgcc ccagaccctg         550 gtggtggggc tcctgaagca aggcctggct ggggcaggct ggagggcaaa          600
gacgctcatt gccctggctt gggctccctt cctctgagat cctgaggata          650
gtctgaggca ggcccagaga gggactcagg tttcttatgg aagggcttct          700
cattcatccc taatataatc cttgcaatga ccc                            733
```